(12) United States Patent
Smith et al.

(10) Patent No.: US 11,389,301 B2
(45) Date of Patent: Jul. 19, 2022

(54) VERTEBRAL BODY REPLACEMENT AND INSERTION METHODS

(71) Applicant: NuVasive, Inc., San Diego, CA (US)

(72) Inventors: William D. Smith, Las Vegas, NV (US); Benjamin Arnold, San Diego, CA (US); Daniel Zatta, San Diego, CA (US); Jeremy Malik, San Diego, CA (US); Morton B. Albert, Carlsbad, CA (US)

(73) Assignee: NuVasive, Inc., San Diego, CA (US)

( * ) Notice: Subject to any disclaimer, the term of this patent is extended or adjusted under 35 U.S.C. 154(b) by 464 days.

(21) Appl. No.: 16/661,922

(22) Filed: Oct. 23, 2019

(65) Prior Publication Data

US 2020/0054459 A1    Feb. 20, 2020

Related U.S. Application Data

(63) Continuation of application No. 15/645,866, filed on Jul. 10, 2017, now Pat. No. 10,485,672, which is a
(Continued)

(51) Int. Cl.
| | |
|---|---|
| *A61F 2/44* | (2006.01) |
| *A61B 17/02* | (2006.01) |
| *A61F 2/46* | (2006.01) |
| *A61F 2/30* | (2006.01) |
| *A61B 90/00* | (2016.01) |

(52) U.S. Cl.
CPC ............. *A61F 2/44* (2013.01); *A61B 17/025* (2013.01); *A61F 2/4611* (2013.01); *A61F 2/4637* (2013.01); *A61B 2017/0256* (2013.01); *A61B 2090/061* (2016.02); *A61F 2002/3008* (2013.01); *A61F 2002/30387* (2013.01); *A61F 2002/30593* (2013.01); *A61F 2002/30604* (2013.01); *A61F 2002/443* (2013.01); *A61F 2002/4627* (2013.01);
(Continued)

(58) Field of Classification Search
CPC ...................................... A61F 2/44–2002/4495
See application file for complete search history.

(56) References Cited

U.S. PATENT DOCUMENTS

| | | |
|---|---|---|
| 4,657,550 A | 4/1987 | Daher |
| 4,759,766 A | 7/1988 | Buettner-Janz |

(Continued)

FOREIGN PATENT DOCUMENTS

| | | |
|---|---|---|
| AU | 2001288840 B2 | 2/2008 |
| AU | 2008202235 A1 | 6/2008 |

(Continued)

*Primary Examiner* — Zade Coley
(74) *Attorney, Agent, or Firm* — Hoffman Warnick LLC

(57) ABSTRACT

A vertebral body replacement device, dimensioned for implantation between a first and second vertebral bone is described. The vertebral body replacement device includes a superior endcap, an inferior endcap and a central core between the superior and inferior endcaps. The vertebral body replacement device further includes a fusion aperture extending through the superior and inferior endcaps and central core. The vertebral body replacement device is made of radiolucent material and can be implanted from a lateral or anterior approach to the spine.

20 Claims, 24 Drawing Sheets

Related U.S. Application Data continuation of application No. 13/425,380, filed on Mar. 20, 2012, now Pat. No. 9,700,425.

(60) Provisional application No. 61/454,571, filed on Mar. 20, 2011.

(52) U.S. Cl.
CPC ............... *A61F 2002/4628* (2013.01); *A61F 2002/4629* (2013.01); *A61F 2002/4658* (2013.01)

(56) References Cited

U.S. PATENT DOCUMENTS

| | | | |
|---|---|---|---|
| 5,171,278 A | 12/1992 | Pisharodi | |
| 5,192,327 A | 3/1993 | Brantigan | |
| 5,236,460 A | 8/1993 | Barber | |
| 5,290,312 A | 3/1994 | Kojimoto | |
| 5,360,430 A | 11/1994 | Lin | |
| 5,390,683 A | 2/1995 | Pisharodi | |
| 5,405,391 A | 4/1995 | Hednerson | |
| 5,458,641 A | 10/1995 | Ramirez | |
| 5,496,712 A | 3/1996 | Cappello | |
| 5,514,180 A | 5/1996 | Heggeness | |
| 5,514,581 A | 5/1996 | Ferrari | |
| 5,522,899 A | 6/1996 | Michelson | |
| 5,534,029 A | 7/1996 | Shima | |
| 5,571,190 A | 11/1996 | Ulrich | |
| 5,571,192 A | 11/1996 | Schonhoffer | |
| 5,606,019 A | 2/1997 | Cappello | |
| 5,641,648 A | 6/1997 | Ferrari | |
| 5,702,454 A | 12/1997 | Baumgartner | |
| 5,723,588 A | 3/1998 | Donofrio | |
| 5,760,004 A | 6/1998 | Stedronsky | |
| 5,770,697 A | 6/1998 | Ferrari | |
| 5,773,577 A | 6/1998 | Cappello | |
| 5,776,198 A * | 7/1998 | Rabbe | A61F 2/44 606/264 |
| 5,776,199 A | 7/1998 | Michelson | |
| 5,916,267 A | 6/1999 | Tienboon | |
| 5,989,290 A | 11/1999 | Biedermann | |
| 6,066,175 A | 5/2000 | Henderson | |
| 6,086,613 A | 7/2000 | Camino | |
| 6,106,557 A * | 8/2000 | Robioneck | A61F 2/44 606/907 |
| 6,110,210 A | 8/2000 | Norton | |
| 6,140,072 A | 10/2000 | Ferrari | |
| 6,159,211 A | 12/2000 | Boriani | |
| 6,174,311 B1 | 1/2001 | Branch | |
| 6,174,334 B1 | 1/2001 | Suddaby | |
| 6,176,880 B1 | 1/2001 | Plouhar | |
| 6,176,882 B1 * | 1/2001 | Biedermann | A61F 2/447 623/17.11 |
| 6,184,348 B1 | 2/2001 | Ferrari | |
| 6,190,413 B1 | 2/2001 | Sutcliffe | |
| 6,200,347 B1 | 3/2001 | Anderson | |
| 6,210,162 B1 | 4/2001 | Chishti | |
| 6,235,043 B1 | 5/2001 | Reiley | |
| 6,245,107 B1 | 6/2001 | Ferree | |
| 6,245,108 B1 | 6/2001 | Biscup | |
| 6,248,110 B1 | 6/2001 | Reiley | |
| 6,251,140 B1 | 6/2001 | Marino | |
| 6,258,125 B1 | 7/2001 | Paul | |
| 6,258,872 B1 | 7/2001 | Stedronsky | |
| 6,296,647 B1 | 10/2001 | Robioneck | |
| 6,309,215 B1 | 10/2001 | Phan | |
| 6,332,895 B1 | 12/2001 | Suddaby | |
| 6,375,681 B1 | 4/2002 | Truscott | |
| 6,375,683 B1 | 4/2002 | Crozet | |
| 6,380,154 B1 | 4/2002 | Cappello | |
| 6,387,130 B1 | 5/2002 | Stone | |
| 6,395,030 B1 | 5/2002 | Songer | |
| 6,402,750 B1 | 6/2002 | Atkinson | |
| 6,402,785 B1 | 6/2002 | Zdeblick | |
| 6,419,704 B1 | 7/2002 | Ferree | |
| 6,423,333 B1 | 7/2002 | Stedronsky | |
| 6,432,107 B1 | 8/2002 | Ferree | |
| 6,447,547 B1 | 9/2002 | Michelson | |
| 6,454,806 B1 | 9/2002 | Cohen | |
| 6,468,311 B2 | 10/2002 | Boyd | |
| 6,558,424 B2 | 5/2003 | Thalgott | |
| 6,579,321 B1 | 6/2003 | Gordon | |
| 6,595,998 B2 | 7/2003 | Johnson | |
| 6,616,695 B1 | 9/2003 | Crozet | |
| 6,632,246 B1 | 10/2003 | Simon | |
| 6,679,914 B1 | 1/2004 | Gabbay | |
| 6,719,794 B2 | 4/2004 | Gerber | |
| 6,723,096 B1 | 4/2004 | Dorchak | |
| 6,726,720 B2 | 4/2004 | Ross | |
| 6,730,088 B2 | 5/2004 | Yeh | |
| 6,740,093 B2 | 5/2004 | Hochschuler | |
| 6,758,862 B2 | 7/2004 | Berry | |
| 6,761,738 B1 | 7/2004 | Boyd | |
| 6,764,514 B1 | 7/2004 | Li | |
| 6,776,860 B2 | 8/2004 | Arai | |
| 6,783,546 B2 | 8/2004 | Zucherman | |
| 6,808,538 B2 | 10/2004 | Paponneau | |
| 6,852,126 B2 | 2/2005 | Ahlgren | |
| 6,855,167 B2 | 2/2005 | Shimp | |
| 6,899,734 B2 | 5/2005 | Castro | |
| 6,899,735 B2 | 5/2005 | Coates | |
| 6,936,070 B1 | 8/2005 | Muhanna | |
| 6,942,475 B2 | 9/2005 | Ensign | |
| 6,942,697 B2 | 9/2005 | Lange | |
| 6,969,404 B2 | 11/2005 | Ferree | |
| 6,974,480 B2 | 12/2005 | Messerli | |
| 6,981,990 B2 | 1/2006 | Keller | |
| 6,986,772 B2 | 1/2006 | Michelson | |
| 6,997,929 B2 | 2/2006 | Manzi | |
| 7,001,433 B2 | 2/2006 | Songer | |
| 7,004,945 B2 | 2/2006 | Boyd | |
| 7,018,413 B2 | 3/2006 | Krüger | |
| 7,037,339 B2 | 5/2006 | Houfburg | |
| 7,044,968 B1 | 5/2006 | Yaccarino | |
| 7,048,762 B1 | 5/2006 | Sander | |
| 7,048,765 B1 | 5/2006 | Grooms | |
| 7,118,579 B2 | 10/2006 | Michelson | |
| 7,153,325 B2 | 12/2006 | Kim | |
| 7,166,110 B2 | 1/2007 | Yundt | |
| 7,182,782 B2 | 2/2007 | Kirschman | |
| 7,192,447 B2 | 3/2007 | Rhoda | |
| 7,208,222 B2 | 4/2007 | Rolfe | |
| 7,211,112 B2 | 5/2007 | Baynham | |
| 7,235,101 B2 * | 6/2007 | Berry | A61F 2/4455 623/17.14 |
| 7,238,206 B2 | 7/2007 | Lange | |
| 7,241,303 B2 | 7/2007 | Reiss | |
| 7,252,685 B2 | 8/2007 | Bindseil | |
| 7,252,686 B2 | 8/2007 | Carrison | |
| 7,255,714 B2 | 8/2007 | Malek | |
| 7,261,720 B2 | 8/2007 | Stevens | |
| 7,267,690 B2 | 9/2007 | Felt | |
| 7,270,682 B2 | 9/2007 | Frigg | |
| 7,273,497 B2 | 9/2007 | Ferree | |
| 7,285,134 B2 | 10/2007 | Berry | |
| 7,300,465 B2 | 11/2007 | Paul | |
| 7,309,358 B2 | 12/2007 | Berry | |
| 7,344,468 B2 | 3/2008 | Chuo | |
| 7,344,564 B2 | 3/2008 | Sweeney | |
| 7,351,262 B2 | 4/2008 | Bindseil | |
| 7,361,192 B2 | 4/2008 | Doty | |
| 7,435,261 B1 | 10/2008 | Castro | |
| 7,491,240 B1 | 2/2009 | Carver | |
| 7,491,268 B2 | 2/2009 | Hoffis | |
| 7,537,612 B2 | 5/2009 | Kunzler | |
| 7,537,617 B2 | 5/2009 | Bindsell | |
| 7,563,281 B2 | 7/2009 | Sears | |
| 7,575,577 B2 | 8/2009 | Boyd | |
| 7,578,848 B2 | 8/2009 | Albert | |
| 7,591,852 B2 | 9/2009 | Prosser | |
| 7,601,157 B2 | 10/2009 | Boyd | |
| 7,615,052 B2 | 11/2009 | Serbousek | |
| 7,615,078 B2 | 11/2009 | White | |

(56) References Cited

U.S. PATENT DOCUMENTS

| | | | | |
|---|---|---|---|---|
| 7,618,458 | B2 | 11/2009 | Biedermann | |
| 7,621,953 | B2 | 11/2009 | Braddock | |
| 7,641,701 | B2 | 1/2010 | Kirschman | |
| 7,655,046 | B2 | 2/2010 | Dryer | |
| 7,666,227 | B2 | 2/2010 | Schaller | |
| 7,682,394 | B2 | 3/2010 | Recoules-Arche | |
| 7,682,397 | B2 | 3/2010 | Berry | |
| 7,690,381 | B2 | 4/2010 | Bartish | |
| 7,695,515 | B2 | 4/2010 | Sweeney | |
| 7,717,959 | B2 * | 5/2010 | William | A61F 2/4425 623/17.15 |
| 7,722,623 | B2 | 5/2010 | Franks | |
| 7,722,674 | B1 | 5/2010 | Grotz | |
| 7,731,751 | B2 | 6/2010 | Butler | |
| 7,731,752 | B2 | 6/2010 | Edie | |
| 7,753,912 | B2 | 7/2010 | Raymond | |
| 7,753,958 | B2 | 7/2010 | Gordon | |
| 7,803,188 | B2 | 9/2010 | Justis | |
| 7,803,192 | B2 | 9/2010 | Oh | |
| 7,806,914 | B2 | 10/2010 | Boyd | |
| 7,815,683 | B2 | 10/2010 | Melkent | |
| 7,825,083 | B2 | 11/2010 | Carter | |
| 7,828,846 | B2 | 11/2010 | Biedermann | |
| 7,829,297 | B2 | 11/2010 | Spector | |
| 7,850,733 | B2 | 12/2010 | Baynham | |
| 7,862,617 | B2 | 1/2011 | Lamprich | |
| 7,862,618 | B2 | 1/2011 | White | |
| 7,875,078 | B2 | 1/2011 | Wysocki | |
| 7,887,593 | B2 | 2/2011 | McKay | |
| 7,887,596 | B2 | 2/2011 | Douget | |
| 7,893,229 | B2 | 2/2011 | Ferrari | |
| 7,905,920 | B2 | 3/2011 | Galea | |
| 7,918,874 | B2 | 4/2011 | Siegal | |
| 7,938,858 | B2 | 5/2011 | Miller | |
| 7,967,866 | B2 | 6/2011 | Dewey | |
| 7,967,867 | B2 * | 6/2011 | Barreiro | A61F 2/4455 623/17.15 |
| 7,972,382 | B2 | 7/2011 | Foley | |
| 7,993,375 | B2 | 8/2011 | Bae | |
| 8,002,833 | B2 | 8/2011 | Fabris Monterumici | |
| 8,021,429 | B2 | 9/2011 | Viker | |
| 8,034,109 | B2 | 10/2011 | Zwirkoski | |
| 8,034,111 | B2 | 10/2011 | Hsu | |
| 8,057,546 | B2 | 11/2011 | Studer | |
| 8,062,367 | B2 | 11/2011 | Kirschman | |
| 8,070,817 | B2 | 12/2011 | Gradl | |
| 8,075,581 | B2 | 12/2011 | Thramann | |
| 8,080,061 | B2 | 12/2011 | Appenzeller | |
| 8,092,536 | B2 | 1/2012 | Ahrens | |
| 8,100,978 | B2 | 1/2012 | Bass | |
| 8,105,328 | B2 | 1/2012 | Protopsaltis | |
| 8,110,004 | B2 | 2/2012 | Valdevit | |
| 8,128,701 | B2 | 3/2012 | Kast | |
| 8,137,401 | B2 | 3/2012 | Stad | |
| 8,142,437 | B2 | 3/2012 | McLean | |
| 8,147,524 | B2 | 4/2012 | Piza Vallespir | |
| 8,152,849 | B2 | 4/2012 | Biedermann | |
| 8,152,852 | B2 | 4/2012 | Biyani | |
| 8,162,990 | B2 | 4/2012 | Potash | |
| 8,163,026 | B2 | 4/2012 | Gray | |
| 8,177,846 | B2 | 5/2012 | Blackwell | |
| 8,197,544 | B1 | 6/2012 | Manzi | |
| 8,202,321 | B2 | 6/2012 | Gerner | |
| 8,206,423 | B2 | 6/2012 | Siegal | |
| 8,236,055 | B2 | 8/2012 | Cordaro | |
| 8,241,294 | B2 | 8/2012 | Sommerich | |
| 8,241,362 | B2 | 8/2012 | Voorhies | |
| 8,241,363 | B2 | 8/2012 | Sommerich | |
| 8,246,683 | B2 | 8/2012 | Castro | |
| 8,267,939 | B2 | 9/2012 | Cipoletti | |
| 8,273,126 | B2 | 9/2012 | Lindner | |
| 8,291,572 | B2 | 10/2012 | Grooms | |
| 8,298,287 | B2 | 10/2012 | Moumene | |
| 8,337,532 | B1 | 12/2012 | McLean | |
| 8,337,558 | B2 | 12/2012 | Lindner | |
| 8,357,168 | B2 | 1/2013 | Wilson | |
| 8,366,776 | B2 | 2/2013 | Heinz | |
| 8,372,120 | B2 | 2/2013 | James | |
| 8,372,152 | B2 | 2/2013 | Kirschman | |
| 8,377,140 | B2 | 2/2013 | DeFalco | |
| 8,382,842 | B2 | 2/2013 | Greenhalgh | |
| 8,394,108 | B2 | 3/2013 | McLean | |
| 8,414,649 | B1 | 4/2013 | Zielinski | |
| 8,425,606 | B2 | 4/2013 | Cowan | |
| 8,430,913 | B2 | 4/2013 | James | |
| 8,454,617 | B2 | 6/2013 | Schaller | |
| 8,454,664 | B2 | 6/2013 | McLean | |
| 8,465,524 | B2 | 6/2013 | Siegal | |
| 8,491,639 | B2 | 7/2013 | James | |
| 8,491,657 | B2 | 7/2013 | Attia | |
| 8,540,772 | B2 | 9/2013 | Osman | |
| 8,545,561 | B2 | 10/2013 | Blacklock | |
| 8,545,567 | B1 | 10/2013 | Krueger | |
| 8,568,483 | B2 | 10/2013 | Coppes | |
| 8,585,761 | B2 | 11/2013 | Theofilos | |
| 8,613,770 | B2 | 12/2013 | Lei | |
| 8,632,591 | B2 | 1/2014 | Vila | |
| 8,641,769 | B2 | 2/2014 | Malandain | |
| 8,657,481 | B2 | 2/2014 | Collins | |
| 8,673,006 | B2 | 3/2014 | Castro | |
| 8,685,099 | B2 | 4/2014 | Bhattacharya | |
| 8,690,883 | B2 | 4/2014 | Collins | |
| 8,690,950 | B2 | 4/2014 | Refai | |
| 8,753,399 | B2 | 6/2014 | Sharifi-Mehr | |
| 8,771,355 | B2 | 7/2014 | Abdou | |
| 8,771,357 | B2 | 7/2014 | Biedermann | |
| 8,777,954 | B2 | 7/2014 | McLean | |
| 8,795,374 | B2 | 8/2014 | Chee | |
| 8,821,577 | B2 | 9/2014 | Pointillart | |
| 8,858,227 | B2 | 10/2014 | Chishti | |
| 8,915,964 | B2 | 12/2014 | Overes | |
| 2001/0039456 | A1 | 11/2001 | Boyer | |
| 2002/0099444 | A1 * | 7/2002 | Boyd | A61F 2/4455 623/23.76 |
| 2002/0106393 | A1 | 8/2002 | Bianchi | |
| 2002/0138143 | A1 | 9/2002 | Grooms | |
| 2002/0165550 | A1 * | 11/2002 | Frey | A61B 17/1671 606/85 |
| 2003/0004574 | A1 | 1/2003 | Ferree | |
| 2003/0032963 | A1 | 2/2003 | Reiss | |
| 2003/0069639 | A1 | 4/2003 | Sander | |
| 2003/0083746 | A1 | 5/2003 | Kuslich | |
| 2003/0171812 | A1 | 9/2003 | Grunberg | |
| 2003/0176924 | A1 | 9/2003 | Burdett | |
| 2003/0199980 | A1 | 10/2003 | Siedler | |
| 2003/0233145 | A1 * | 12/2003 | Landry | A61F 2/4657 606/100 |
| 2004/0002758 | A1 | 1/2004 | Landry | |
| 2004/0034430 | A1 * | 2/2004 | Falahee | A61F 2/4455 623/17.16 |
| 2004/0049270 | A1 | 3/2004 | Gewirtz | |
| 2004/0133278 | A1 | 7/2004 | Marino | |
| 2004/0133279 | A1 | 7/2004 | Krueger | |
| 2004/0153160 | A1 | 8/2004 | Carrasco | |
| 2004/0186569 | A1 | 9/2004 | Berry | |
| 2004/0186570 | A1 | 9/2004 | Rapp | |
| 2004/0193270 | A1 | 9/2004 | DiMauro | |
| 2004/0210312 | A1 * | 10/2004 | Neumann | A61F 2/44 623/17.11 |
| 2005/0027359 | A1 * | 2/2005 | Mashburn | A61F 2/4465 623/17.11 |
| 2005/0060034 | A1 * | 3/2005 | Berry | A61F 2/44 623/17.14 |
| 2005/0060036 | A1 | 3/2005 | Schumacher | |
| 2005/0107878 | A1 | 5/2005 | Conchy | |
| 2005/0113924 | A1 | 5/2005 | Buttermann | |
| 2005/0124999 | A1 | 6/2005 | Teitelbaum | |
| 2005/0143737 | A1 | 6/2005 | Pafford | |
| 2005/0149035 | A1 * | 7/2005 | Pimenta | A61B 17/02 606/86 R |
| 2005/0165484 | A1 | 7/2005 | Ferree | |
| 2005/0165485 | A1 * | 7/2005 | Trieu | A61F 2/442 623/17.13 |

(56) References Cited

U.S. PATENT DOCUMENTS

| | | |
|---|---|---|
| 2005/0177237 A1 | 8/2005 | Shappley |
| 2005/0182412 A1 | 8/2005 | Johnson |
| 2005/0187625 A1 | 8/2005 | Wolek |
| 2005/0209555 A1 | 9/2005 | Middleton |
| 2005/0256582 A1* | 11/2005 | Ferree ............... A61B 17/7059 623/17.11 |
| 2005/0283245 A1 | 12/2005 | Gordon |
| 2006/0015182 A1 | 1/2006 | Tsou |
| 2006/0015183 A1 | 1/2006 | Gilbert |
| 2006/0015184 A1 | 1/2006 | Winterbottom |
| 2006/0058879 A1 | 3/2006 | Metz-Stavenhagen |
| 2006/0064168 A1 | 3/2006 | Keller |
| 2006/0069441 A1 | 3/2006 | Zucherman |
| 2006/0106462 A1 | 5/2006 | Tsou |
| 2006/0122701 A1 | 6/2006 | Kiester |
| 2006/0129244 A1 | 6/2006 | Ensign |
| 2006/0195192 A1 | 8/2006 | Gordon |
| 2006/0204966 A1 | 9/2006 | Spector |
| 2006/0217747 A1 | 9/2006 | Ferree |
| 2006/0247665 A1 | 11/2006 | Ferree |
| 2006/0253202 A1 | 11/2006 | Lipov |
| 2006/0259144 A1* | 11/2006 | Trieu ...................... A61F 2/442 623/17.13 |
| 2006/0265077 A1 | 11/2006 | Zwirkoski |
| 2006/0293663 A1 | 12/2006 | Walkenhorst |
| 2007/0027471 A1 | 2/2007 | Ferree |
| 2007/0032791 A1 | 2/2007 | Greenhalgh |
| 2007/0032874 A1* | 2/2007 | Lee ....................... A61F 2/0811 623/17.13 |
| 2007/0050030 A1 | 3/2007 | Kim |
| 2007/0088436 A1 | 4/2007 | Parsons |
| 2007/0093689 A1 | 4/2007 | Steinberg |
| 2007/0093903 A1 | 4/2007 | Cheng |
| 2007/0100212 A1* | 5/2007 | Pimenta ............ A61B 17/0206 600/210 |
| 2007/0118129 A1 | 5/2007 | Fraser |
| 2007/0118130 A1 | 5/2007 | O'Neil |
| 2007/0123987 A1 | 5/2007 | Bernstein |
| 2007/0149978 A1 | 6/2007 | Shezifi |
| 2007/0173941 A1* | 7/2007 | Allard .................. A61F 2/4425 623/17.14 |
| 2007/0179615 A1* | 8/2007 | Heinz .................. A61F 2/4425 623/17.14 |
| 2007/0179618 A1* | 8/2007 | Trieu .................... A61F 2/4425 623/17.14 |
| 2007/0208227 A1* | 9/2007 | Smith .................... A61B 17/02 600/219 |
| 2007/0233246 A1* | 10/2007 | Trieu ..................... A61F 2/442 623/17.11 |
| 2007/0233272 A1 | 10/2007 | Boyce |
| 2007/0239158 A1 | 10/2007 | Trieu |
| 2007/0260318 A1 | 11/2007 | Lawson |
| 2007/0270968 A1* | 11/2007 | Baynham ............... A61F 2/447 623/17.11 |
| 2007/0276491 A1 | 11/2007 | Ahrens |
| 2007/0288092 A1 | 12/2007 | Bambakidis |
| 2008/0004704 A1 | 1/2008 | Katz |
| 2008/0039942 A1 | 2/2008 | Bergeron |
| 2008/0045897 A1 | 2/2008 | Collins |
| 2008/0077246 A1 | 3/2008 | Fehling |
| 2008/0119853 A1 | 5/2008 | Felt |
| 2008/0133017 A1 | 6/2008 | Beyar |
| 2008/0154379 A1* | 6/2008 | Steiner ................. A61F 2/4455 623/17.16 |
| 2008/0221586 A1* | 9/2008 | Garcia-Bengochea ........................ A61B 17/34 606/108 |
| 2008/0249628 A1 | 10/2008 | Altarac |
| 2008/0262501 A1 | 10/2008 | Chen |
| 2008/0306599 A1 | 12/2008 | Morrison |
| 2009/0018399 A1* | 1/2009 | Martinelli .............. A61B 5/389 600/210 |
| 2009/0036985 A1 | 2/2009 | Whiting |
| 2009/0076612 A1 | 3/2009 | Reo |
| 2009/0093882 A1 | 4/2009 | Oh |
| 2009/0099569 A1 | 4/2009 | Beger |
| 2009/0105834 A1* | 4/2009 | Hovda ................ A61F 2/30771 623/17.11 |
| 2009/0254180 A1 | 10/2009 | Pazanowski |
| 2009/0292361 A1 | 11/2009 | Lopez |
| 2009/0299478 A1 | 12/2009 | Carls |
| 2009/0326658 A1* | 12/2009 | Allard .................... A61F 2/4425 623/17.16 |
| 2010/0016969 A1 | 1/2010 | Richter |
| 2010/0042219 A1 | 2/2010 | Antonacci |
| 2010/0063510 A1 | 3/2010 | Arlet |
| 2010/0063592 A1 | 3/2010 | Dwyer |
| 2010/0070036 A1* | 3/2010 | Implicito ............... A61F 2/4611 606/191 |
| 2010/0082106 A1 | 4/2010 | Muhanna |
| 2010/0082109 A1 | 4/2010 | Greenhalgh |
| 2010/0094426 A1* | 4/2010 | Grohowski, Jr ........ A61F 2/447 623/17.16 |
| 2010/0125334 A1* | 5/2010 | Krueger ................... A61F 2/442 606/86 R |
| 2010/0137674 A1 | 6/2010 | Evans |
| 2010/0179658 A1 | 7/2010 | Freeman |
| 2010/0191336 A1 | 7/2010 | Greenhalgh |
| 2010/0222750 A1 | 9/2010 | Cheng |
| 2010/0268344 A1 | 10/2010 | de Villiers |
| 2010/0286777 A1 | 11/2010 | Errico |
| 2010/0286778 A1 | 11/2010 | Eisermann |
| 2010/0286779 A1 | 11/2010 | Thibodeau |
| 2010/0286784 A1* | 11/2010 | Curran ................ A61F 2/30771 623/17.16 |
| 2010/0292794 A1 | 11/2010 | Metz-Stavenhagen |
| 2010/0298939 A1 | 11/2010 | Delfosse |
| 2011/0015741 A1 | 1/2011 | Melkent |
| 2011/0035009 A1 | 2/2011 | Sweeney |
| 2011/0097376 A1 | 4/2011 | Berlemann |
| 2011/0106258 A1 | 5/2011 | Blackwell |
| 2011/0106260 A1 | 5/2011 | Laurence |
| 2011/0208306 A1* | 8/2011 | Farris ......................... A61F 2/44 623/17.11 |
| 2011/0218627 A1 | 9/2011 | Rampersaud |
| 2011/0224793 A1 | 9/2011 | Fortin |
| 2011/0257750 A1 | 10/2011 | Barrall |
| 2012/0004730 A1 | 1/2012 | Castro |
| 2012/0029638 A1 | 2/2012 | Miller |
| 2012/0109303 A1 | 5/2012 | Capote |
| 2012/0143334 A1 | 6/2012 | Boyce |
| 2012/0197399 A1 | 8/2012 | Kirschman |
| 2012/0209384 A1 | 8/2012 | Arnold |
| 2012/0226356 A1 | 9/2012 | Hirschl |
| 2012/0276008 A1 | 11/2012 | Walkenhorst |
| 2013/0072978 A1 | 3/2013 | Ammerman |
| 2014/0135931 A1 | 5/2014 | Popa |
| 2014/0142706 A1 | 5/2014 | Hansell |
| 2014/0207239 A1 | 7/2014 | Barreiro |
| 2014/0228874 A1 | 8/2014 | Boyd |
| 2014/0277469 A1 | 9/2014 | Baynham |
| 2014/0277482 A1 | 9/2014 | Gfeller |

FOREIGN PATENT DOCUMENTS

| | | |
|---|---|---|
| BR | 8303394 U | 2/2006 |
| CN | 1053004 A | 7/1991 |
| CN | 1406561 A | 4/2003 |
| CN | 1483389 A | 3/2004 |
| CN | 101019787 A | 8/2007 |
| CN | 201040015 Y | 3/2008 |
| CN | 201216662 Y | 4/2009 |
| CN | 101612070 A | 12/2009 |
| CN | 201445571 U | 5/2010 |
| CN | 101828979 A | 9/2010 |
| CN | 201658439 U | 12/2010 |
| CN | 102240234 A | 11/2011 |
| CN | 1027157969 A | 10/2012 |
| CN | 103300949 A | 9/2013 |
| CN | 203354708 U | 12/2013 |
| CN | 103800101 A | 5/2014 |
| CN | 203591315 U | 5/2014 |

(56) References Cited

FOREIGN PATENT DOCUMENTS

| | | |
|---|---|---|
| CN | 203749650 U | 8/2014 |
| DE | 19519101 A1 | 11/1996 |
| DE | 10127924 C1 | 12/2002 |
| DE | 10357960 A1 | 7/2005 |
| DE | 102004021861 A1 | 11/2005 |
| DE | 202008001260 U1 | 3/2008 |
| DE | 202008001261 U1 | 3/2008 |
| DE | 102007042946 A1 | 12/2008 |
| EP | 0517030 A2 | 9/1996 |
| EP | 1779814 A1 | 5/2007 |
| EP | 1847239 A1 | 10/2007 |
| EP | 1980222 A1 | 10/2008 |
| EP | 2343030 A1 | 7/2011 |
| EP | 2606859 A1 | 6/2013 |
| ES | 2385866 T3 | 10/2005 |
| ES | 2361099 A1 | 5/2008 |
| FR | 2874814 A1 | 3/2006 |
| FR | 2897770 A1 | 8/2007 |
| GB | 2364643 A | 2/2002 |
| JP | 0542168 A | 2/1993 |
| JP | 2005160875 A | 6/2005 |
| KR | 20130007332 A | 1/2013 |
| RU | 2009145504 A | 6/2011 |
| RU | 2009145509 A | 6/2011 |
| WO | WO-1992014423 | 9/1992 |
| WO | WO-1999032055 | 7/1999 |
| WO | WO-2005044151 | 5/2005 |
| WO | WO-2006065932 | 6/2006 |
| WO | WO-2006072941 | 7/2006 |
| WO | WO-2006073402 | 7/2006 |
| WO | WO-2006081843 | 8/2006 |
| WO | WO-2007054952 | 5/2007 |
| WO | WO-2007073488 | 6/2007 |
| WO | WO-2008086192 | 7/2008 |
| WO | WO-2008120215 | 10/2008 |
| WO | WO-2008152499 | 12/2008 |
| WO | WO-2009042672 | 4/2009 |
| WO | WO-2010045901 | 4/2010 |
| WO | WO-2010145627 | 12/2010 |
| WO | WO-2011028236 | 3/2011 |
| WO | WO-2012060877 | 5/2012 |
| WO | WO-2013025448 | 2/2013 |

\* cited by examiner

VERTEBRAL BODY REPLACEMENT AND INSERTION METHODS

CROSS-REFERENCE TO RELATED APPLICATIONS

This application is a continuation of U.S. patent application Ser. No. 15/645,866, filed Jul. 10, 2017, which is a continuation of U.S. patent application Ser. No. 13/425,380 (now U.S. Pat. No. 9,700,425) filed on Mar. 30, 2012, which in turn claimed the benefit of the filing date of U.S. Provisional Application No. 61/454,571, which was filed on Mar. 20, 2011, each of which are hereby incorporated by reference herein as if set forth herein in their entireties.

BACKGROUND OF THE INVENTION

I. Field of the Invention

The present invention relates to spinal implants, implant insertion assemblies, and surgical methods for replacing at least a portion of one or more vertebral bodies of the spine.

II. Discussion of the Prior Art

The spine is formed of a column of vertebra that extends between the cranium and pelvis. The three major sections of the spine are known as the cervical, thoracic and lumbar regions. There are 7 cervical vertebrae, 12 thoracic vertebrae, and 5 lumbar vertebrae, with each of the 24 vertebrae being separated from each other by an intervertebral disc. A series of about 9 fused vertebrae extend from the lumbar region of the spine and make up the pelvic region of the vertebral column. These fused vertebrae consist of the sacral and coccygeal region of the vertebral column.

The main functions of the spine are to provide support and protect the spinal cord. Even slight disruptions to either the intervertebral discs or vertebrae can result in serious discomfort due to decompression of nerve fibers either within the spinal cord or extending from the spinal cord. If a disruption to the spine becomes severe enough, damage to a nerve or part of the spinal cord may occur and can result in partial to total loss of bodily functions (e.g. walking, talking, and breathing). Therefore, it is of great interest and concern to be able to both correct and prevent ailments of the spine.

Trauma to the spine (e.g. car accident, sports injury) can cause fracturing of one or more of the vertebrae. Certain diseases affecting the spine (e.g. tumors, osteoporosis) can cause degeneration of the spine. Both trauma and degeneration may result in severe disruption to the spine. In these circumstances, the complete removal of one or more vertebrae may be required. If one or more vertebrae are removed, a replacement support system must be implanted in order to protect the spinal cord and maintain, or improve, the structure and integrity of the spine.

SUMMARY

According to one broad aspect, a stackable vertebral body replacement is provided comprising variable size upper and lower endcaps and at least one center core, all manufactured from a biocompatible material. For example, the biocompatible material may include, but is not limited to, poly ether ether ketone (PEEK). The upper and lower endcaps comprise a base and a variable height riser connector. The implant endcap has a cavity through the center of the piece to allow for bone fusion. The endcaps connect to the center core by a mating section on one end of the endcap. The mating section allows the endcaps to be joined to opposite ends of the core, and once locked in place they form a complete assembly. The mating section is designed so the vertebral body replacement can be built inside the body or prior to insertion. The endcaps are available in heights ranging from 7 mm to 25 mm and angles ranging from zero to eight degrees, allowing for ideal height reconstruction and restoring lordotic or kyphotic curvature. The center core comprises a body with a hollow center defining a fusion aperture therethrough. Both the top and bottom of this center core comprise mating sections which allow the center core to attach to the endcaps and lock into place. The height of the center core ranges from 10 mm to 80 mm. During lateral insertion, the center core is inserted between the two endcaps using the lateral insertion assembly. If an anterior insertion method is used, either a one-piece vertebral body replacement (endcaps and core body as one complete piece) is inserted or the implant is assembled outside the patient and then inserted as a complete vertebral body replacement.

In one embodiment, the vertebral body replacement is radiolucent. The use of radiolucent material is ideal for use in tumor patients since the surgeon can see through the implant on an x-ray and monitor the site post-surgery. According to this embodiment, radiopaque markers are placed in the endcaps and the core for use in positioning and alignment of the vertebral body replacement during insertion. By way of example only, the radiopaque markers may be titanium or tantalum pins.

The lateral inserter assembly is constructed from a biocompatible material, such as stainless steel. It is comprised of a core insertion tool between two slide retainers held apart by an adjustable clamp. The lateral inserter assembly is used to properly position the endcaps in the body and guide the core between them inside the body. The center core of the vertebral replacement body is attached and removed from the core insertion tool by means of a quick-release on the top of the tool. The two endcaps are attached to the lateral inserter assembly by screwing them onto endcap retaining rods which slide into holes on each side of the slide retainer. The center core is placed between the two slide retainers using the mating sections on the core as a guide between the two slides. Malleting or sliding of the core between the slides provides the distraction of the vertebral bodies without the requirement for an additional device. Once in place, the core insertion tool is detached from the center core using the quick-release and the lateral inserter assembly are unscrewed from the endcaps. This assembly has the advantage of allowing for a smaller opening for access to the spine, compared to previous approaches, which will reduce patient recovery time. Additionally, the stackable assembly provides a slightly lower cost option than expandable cages, while still being able to provide many of the benefits of the lateral approach.

The anterior inserter assembly is used to easily insert the vertebral body replacement into the spinal cavity and release when properly positioned. For anterior insertion the stackable vertebral body replacement (core and two endcaps) are assembled outside the body prior to insertion. The anterior inserter assembly comprises a quick-release to easily affix and detach the vertebral body replacement from the assembly. For the anterior approach, a separate distractor/sizer will be required.

A distractor/sizer assembly is used to open the space between two adjacent vertebrae where the vertebral replacement body will be inserted. The tool is unique since it not only distracts the spinal column, but also measures the desired size of the requirement implant. The distractor/sizer tool comprises two pairs of connected crossed arms with handles at one end (connected by a measurement device) and spreader arms at the other. Opening the space between the handles at one end decreases the distance between the spreader arms at the other end. Affixed to the outside of the spreader arms by a pivoting mount is an endcap with anti-migration elements on the outside face to allow sufficient friction to hold onto the surface of remaining vertebrae during distraction. The vertical distance between the endcaps of the spreader arms can be read from the measurement arm near the handle of the device. The distractor/sizer can accommodate heights from 18 mm to 120 mm.

The lateral method for inserting the stackable vertebral replacement body is as follows: (1) the patient is placed in the lateral decubitus position on the operating table and sedated under general anesthesia, (2) The surgeon ensures proper positioning of the vertebrae to be treated using a fluoroscope, (3) The surgeon makes a small incision in the skin in the patient's side, over the midsection of the disc for a single-level fusion or over the intervening vertebral body for a multi-level fusion, (4) Surgical dissection is performed via the placement of serial dilators, each of which actively provides directional nerve localizing electromyographic (EMG) data to the surgeon for safe navigation near the lumbar nerve plexus. Active neuromonitoring in addition to the use of real-time fluoroscopic guidance insures safety and accuracy as the expandable tubular retractor is carefully advanced through the psoas muscle (for lumbar spine surgeries) to the desired disc space or vertebral body, (5) The endcaps are inserted coupled to the lateral insertion tool, (6) The endcaps are placed into position inside the patient; adjacent the endplates of the vertebral bodies, (7) The clamp holding the two slide retainers is adjusted to the desired width for core insertion, (8) A core is inserted between the two slides and is guided into place between the endcaps, (9) Malleting the core inserter assembly down the slides with the core distraction block attached provides the distraction of the spine. (10) The core is slid down until it locks into place between endcaps, (11) The core is released from the core insertion tool, (12) The insertion tools are removed and the incision is closed.

The anterior method for inserting the stackable vertebral replacement body may be performed as follows: (1) The vertebral body to be replaced is accessed via any anterior approach appropriate for the spinal level, (2) A distractor/sizer is used to distract the endplates of the adjacent vertebral bodies, and to determine the height of the vertebral body replacement (VBR), (3) The vertebral body replacement is built outside the body based on measurements determined from the distractor/sizer and attached to the anterior insertion tool and the distractor/sizer is removed. (4) The inerstion tool is detached from the vertebral body replacement and the anterior insertion tool is removed.

BRIEF DESCRIPTION OF THE DRAWINGS

Many advantages of the present invention will be apparent to those skilled in the art with a reading of this specification in conjunction with the attached drawings, wherein like reference numerals are applied to like elements and wherein.

DETAILED DESCRIPTION

Illustrative embodiments of the invention are described below. In the interest of clarity, not all features of an actual implementation are described in this specification. It will of course be appreciated that in the development of any such actual embodiment, numerous implementation-specific decisions must be made to achieve the developers' specific goals, such as compliance with system-related and business-related constraints, which will vary from one implementation to another. Moreover, it will be appreciated that such a development effort might be complex and time-consuming, but would nevertheless be a routine undertaking for those of ordinary skill in the art having the benefit of this disclosure. The stackable vertebral body replacement, anterior and lateral inserter assemblies, distractor/sizer and methods for implantation disclosed herein boasts a variety of inventive features and components that warrant patent protection, both individually and in combination.

Figure 1:
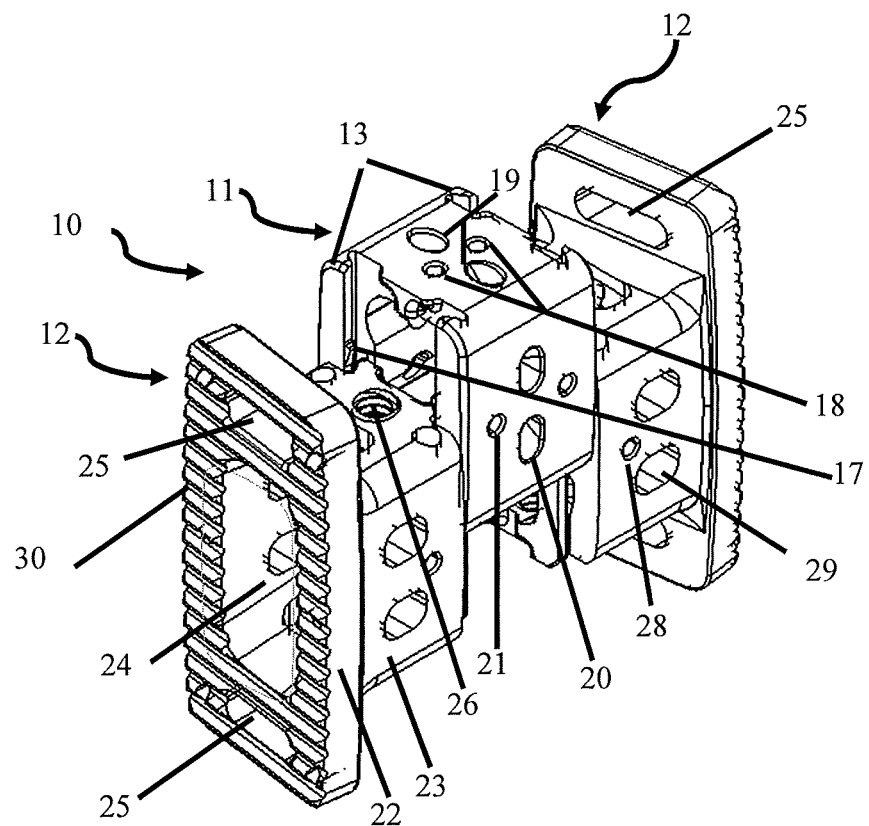
FIG. 1 is the perspective view of a stackable vertebral body replacement according to an exemplary embodiment.
Figure 2:
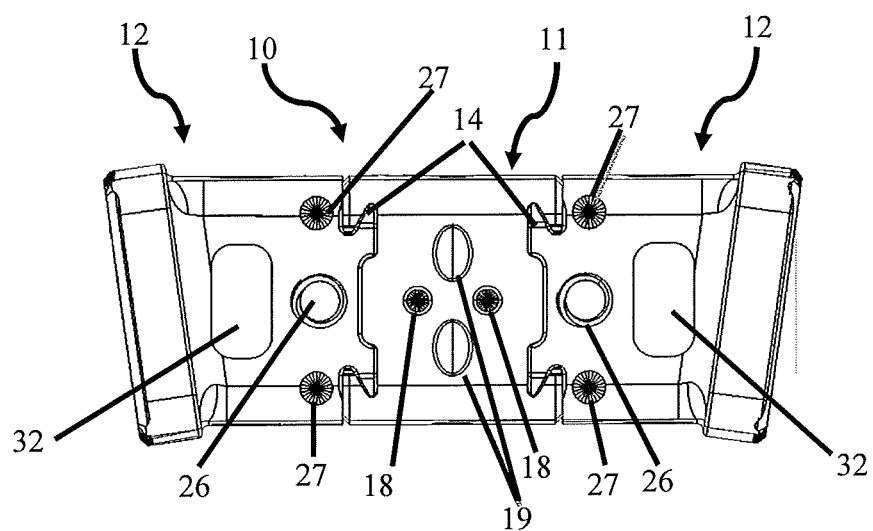
FIG. 2 is the top view of a stackable vertebral body replacement of FIG. 1.
Figure 3:
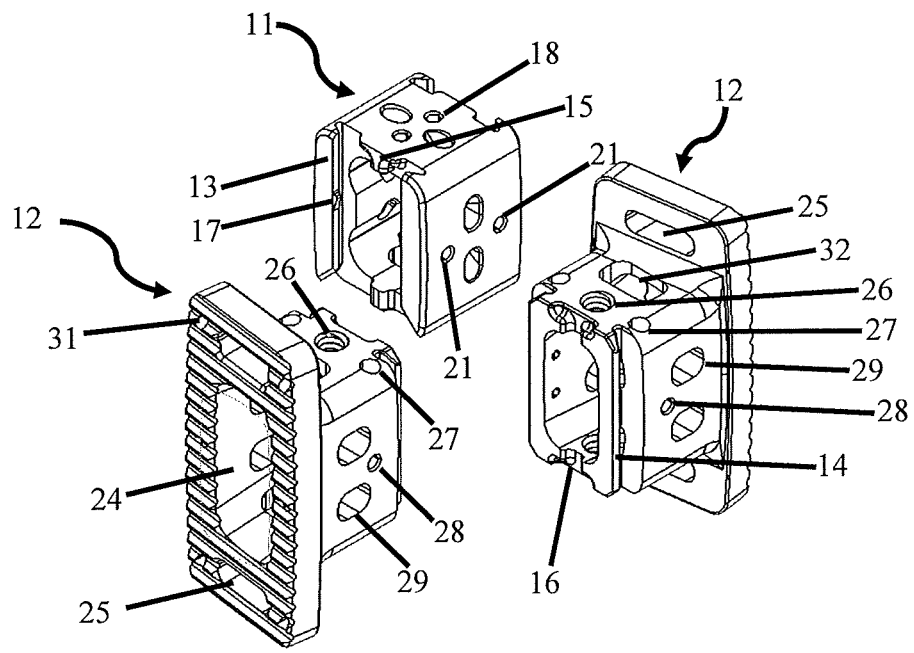
FIG. 3 is an exploded perspective view of the vertebral body replacement of FIG. 1.
Figure 4:
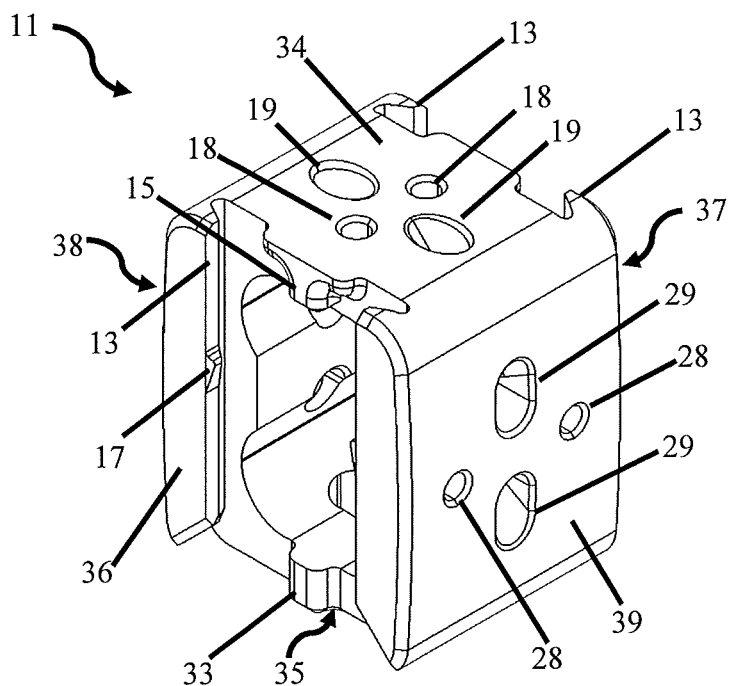
FIG. 4 is a perspective view of the center core section of the vertebral body replacement of FIG. 1.
Figure 5:
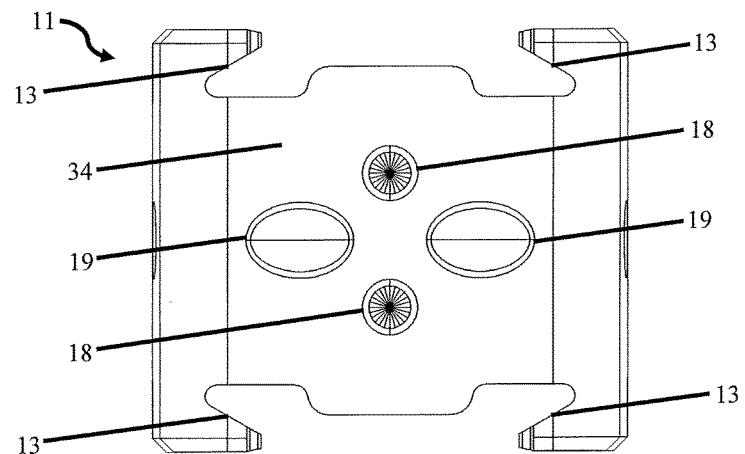
FIG. 5 is the top/bottom view of the core section of the vertebral body replacement implant of FIG. 4.
Figure 6:
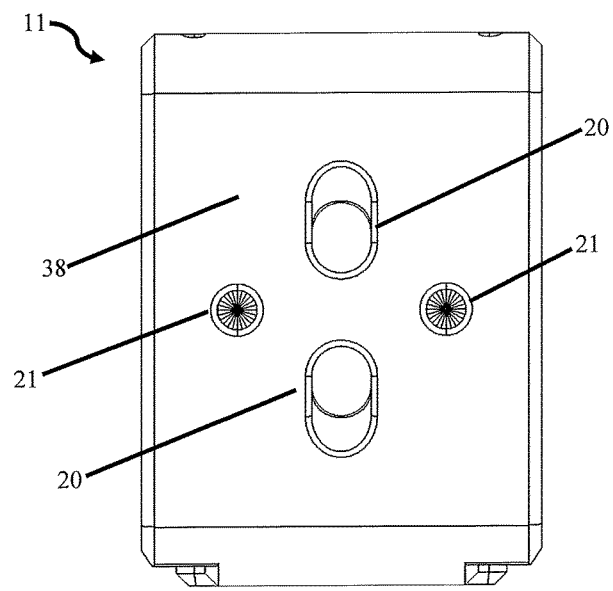
FIG. 6 is the side (left/right) view of the core section of the vertebral body replacement implant of FIG. 4.
Figure 7:
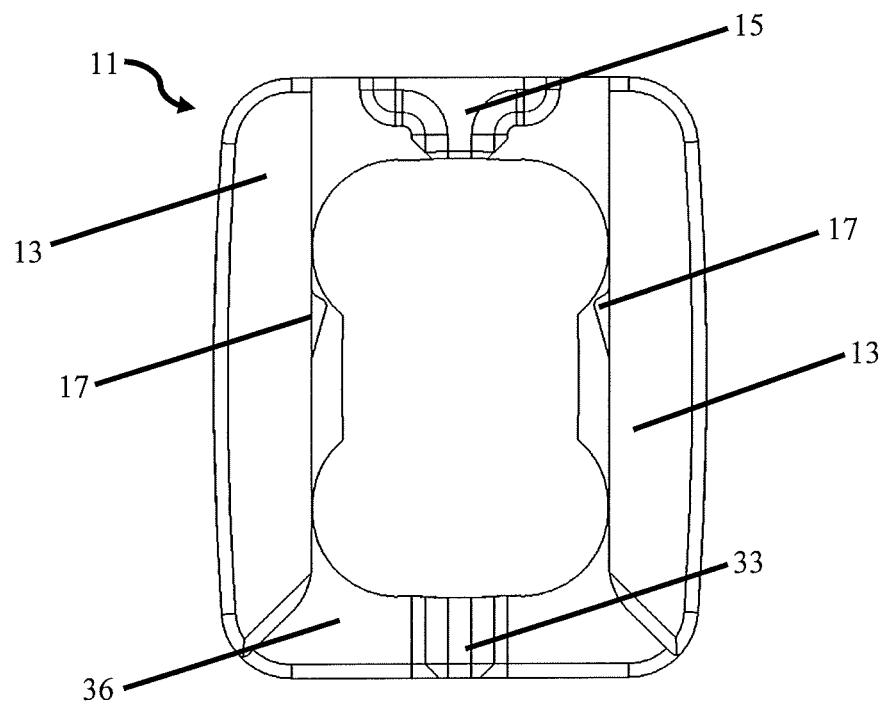
FIG. 7 is the front/back view of the core section of the vertebral body replacement implant of FIG. 4.
Figure 8:
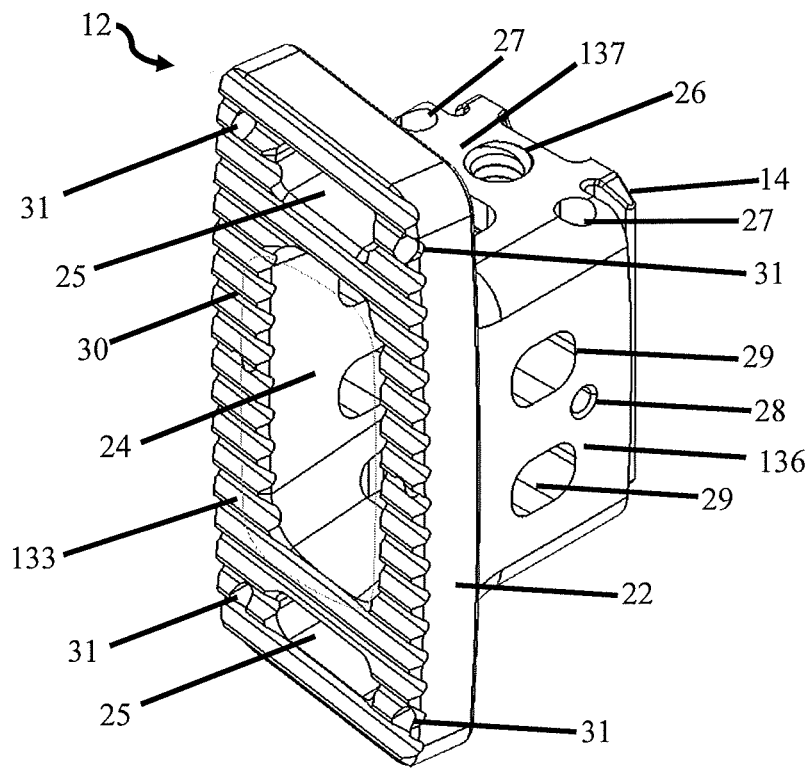
FIG. 8 is the perspective view of an endcap of the vertebral body replacement implant of FIG. 1.
Figure 9:
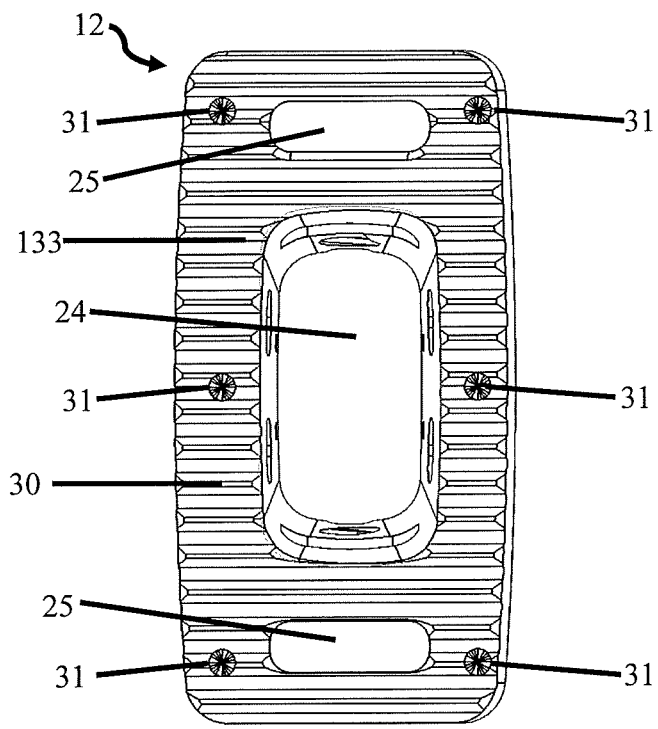
FIG. 9 is the front view of an endcap of the vertebral body replacement implant of FIG. 8.
Figure 10:
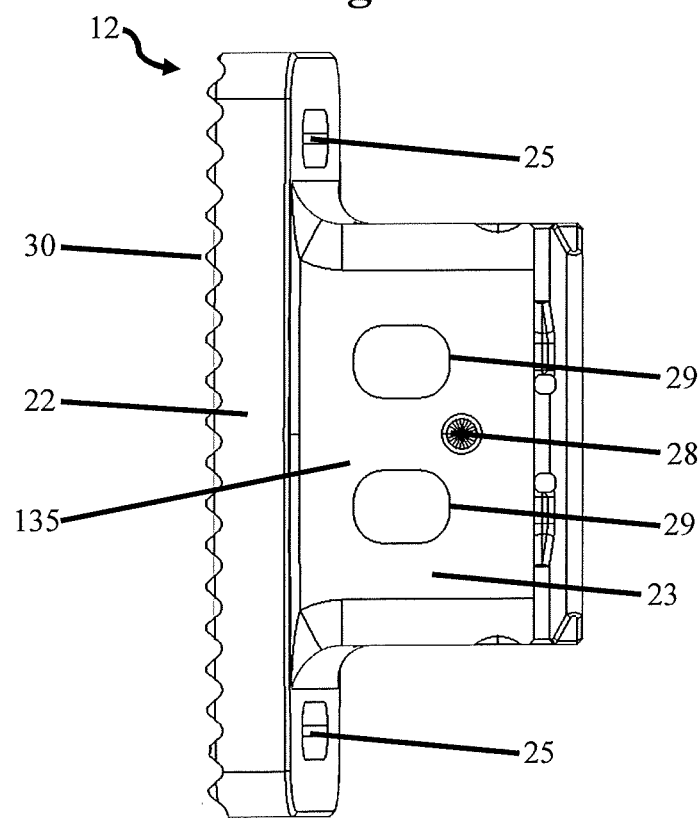
FIG. 10 is the side (left/right) view of the endcap of the vertebral body replacement implant of FIG. 8.
Figure 11:
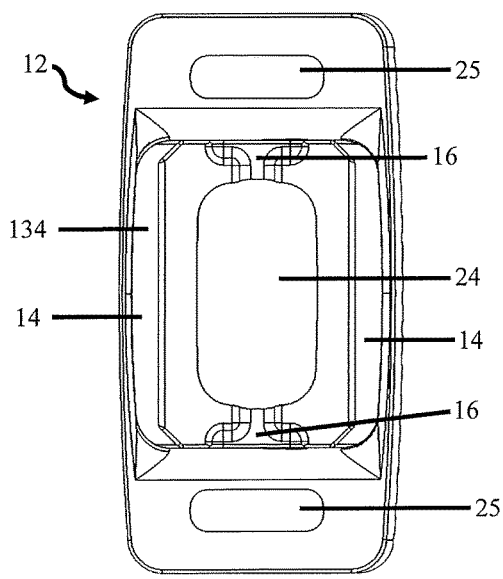
FIG. 11 is the back view of the endcap of the vertebral body replacement implant of FIG. 8.
Figure 12:
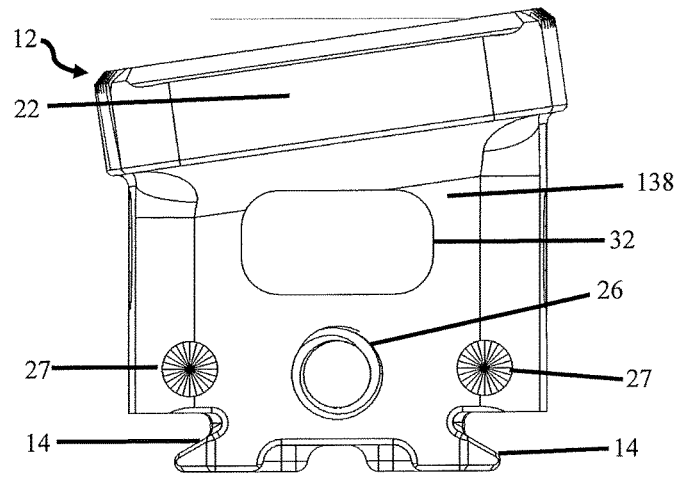
FIG. 12 is the top/bottom view of the endcap of the vertebral body replacement implant of FIG. 8.
Figure 13:
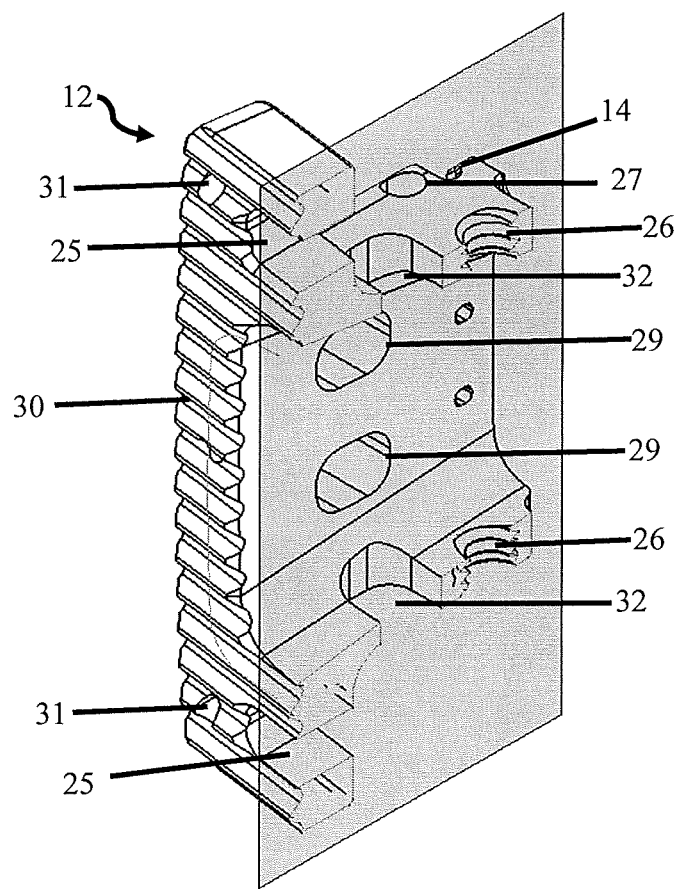
FIG. 13 is the cross-sectional view of the endcap of the vertebral body replacement implant of FIG. 8.

FIGS. 1-13 illustrate an exemplary embodiment of a stackable vertebral body replacement 10 according to one embodiment of the present invention. The stackable vertebral body replacement 10 includes a center core section 11 and two endcaps 12. The core section 11 and the two endcaps 12 are made from a biocompatible material. For example, the components may be machined from implantation-grade polyether ether ketone (PEEK). In one embodiment, six sides comprise the center core 11. The following sides of the core are opposite each other and are identical: top 34 and bottom 35, front 36 and back 37, and left 38 and right 39. The top 34 and bottom 35 sides of the core sections 11 have mating sections 13, which allow the core 11 to couple to the mating sections 14 of the endcaps 12. The core 11 is may vary in height from 10 mm to 80 mm. The core 11 is held in place between the two endcaps 12 by the stops 15 on front 36 and back 37 of the core 11 which lock into the locking assembly 16 on the back of the endcap 12. A guide 33, helps position the core 11 into the mating sections 14 on the endcaps 12 during insertion. Additionally, a protrusion 17 on the mating section 13 increases the friction between the core 11 and endcaps 12 holding the assembly together. The top of the core 11 has holes 18 extending longitudinally therethrough, in which radiopaque markers are placed to verify alignment during insertion. On top of the core 11 there are additional holes 19 which allow entry of the core insertion assembly pins 77 for lateral insertion. The side of the core 11 has holes 20 for attachment to the anterior inserter assembly 90 for anterior insertion. Additional holes 21 in the side of the core 11 allow for insertion of additional radiopaque markers for verifying alignment during insertion.

The endcaps 12 comprise a variable length base 22 and a variable height riser 23. In one embodiment, the endcap base 22 is rectangular with front 133, back 134, left 135, right 136, top 137, and bottom 138 sides. The endcaps 12 range in height from 7 mm to 25 mm. The endcap 12 is comprised of a cavity 24 through the piece which runs from the front 133 to the back 134 to allow for bone fusion through the vertebral body replacement. In one embodiment, in addition to the cavity 24, the endcap base 22 has additional holes 25 which are cut through the base material at opposite ends of the base, also to promote bone fusion with the endcap 12. On the top 137 and bottom 138 of the endcaps 12 are screw holes 26 to allow for connection to the endplate retaining rods 45 of the lateral inserter system 40. Additionally on top 137 and bottom 138 of the endcaps 12 are holes 27 for radiopaque markers for proper alignment during insertion and a hole 32 to promote bone fusion. The side of the implant has an additional hole 28 for a radiopaque marker and holes 29 to promote fusion. The front 133 of the endcap 12 has anti-migration elements 30 designed to grip the ends of the vertebrae after implantation in order to maintain its proper spinal alignment. Additionally, there are a plurality of small holes 31 in the front 133 of the endcap 22, partially through the base for the insertion of radiopaque markers which guide insertion and maintain implant position.

Figure 14:
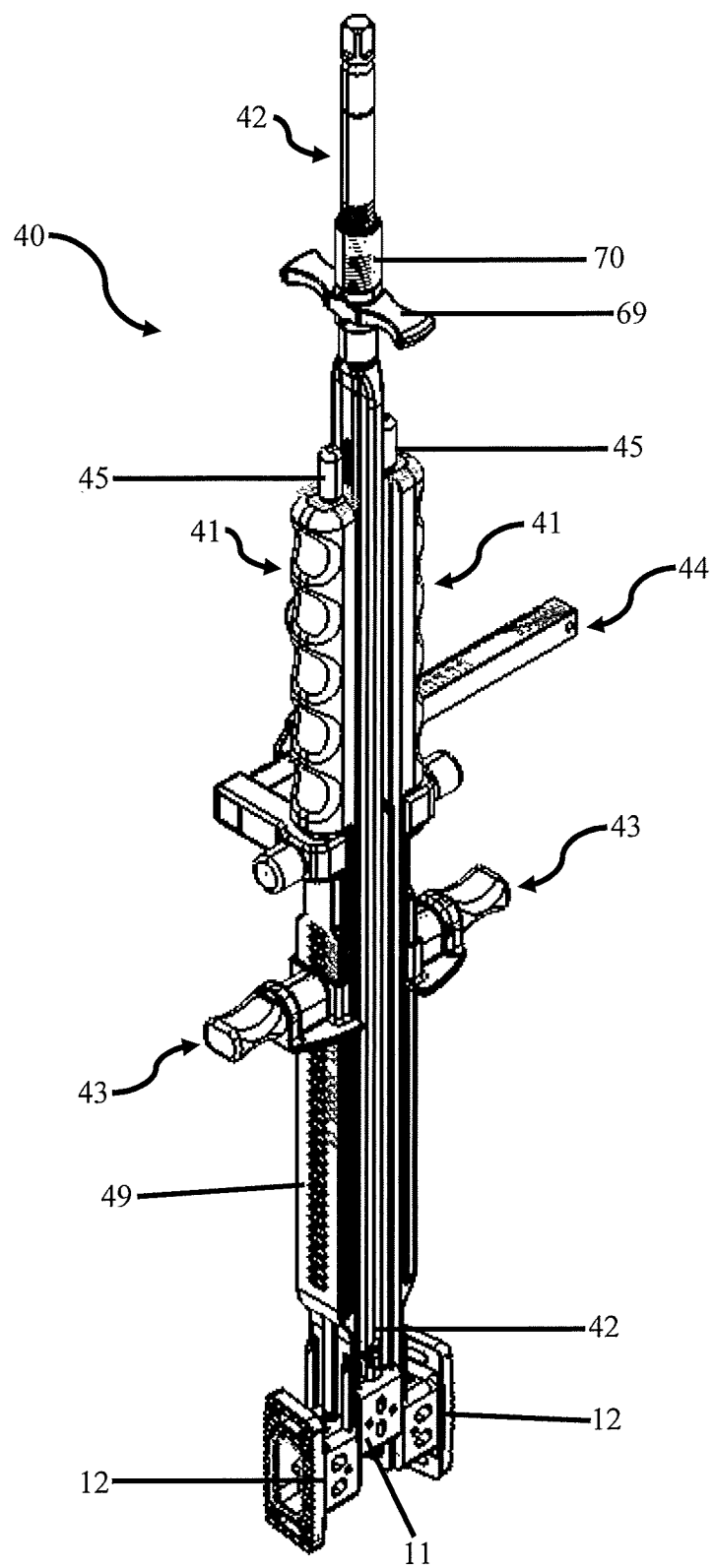
FIG. 14 is the perspective view of the lateral inserter assembly.
Figure 15:
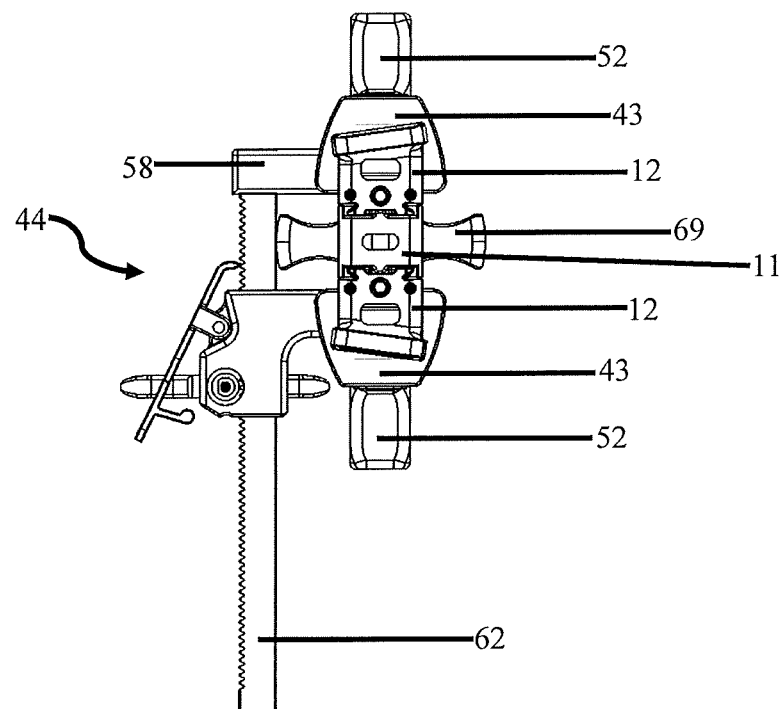
FIG. 15 is the bottom view of the lateral inserter assembly of FIG. 14.
Figure 16:
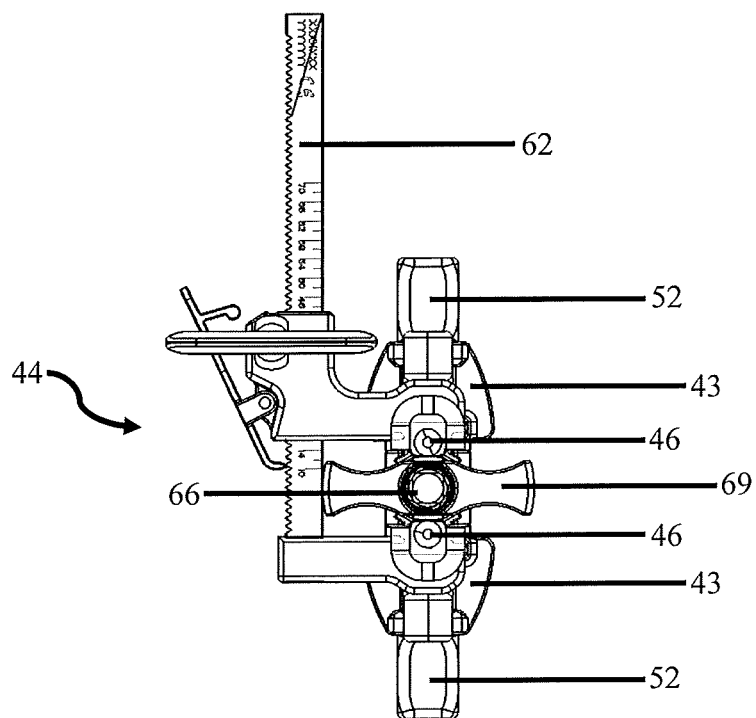
FIG. 16 is the top view of the lateral inserter assembly of FIG. 14.
Figure 17:
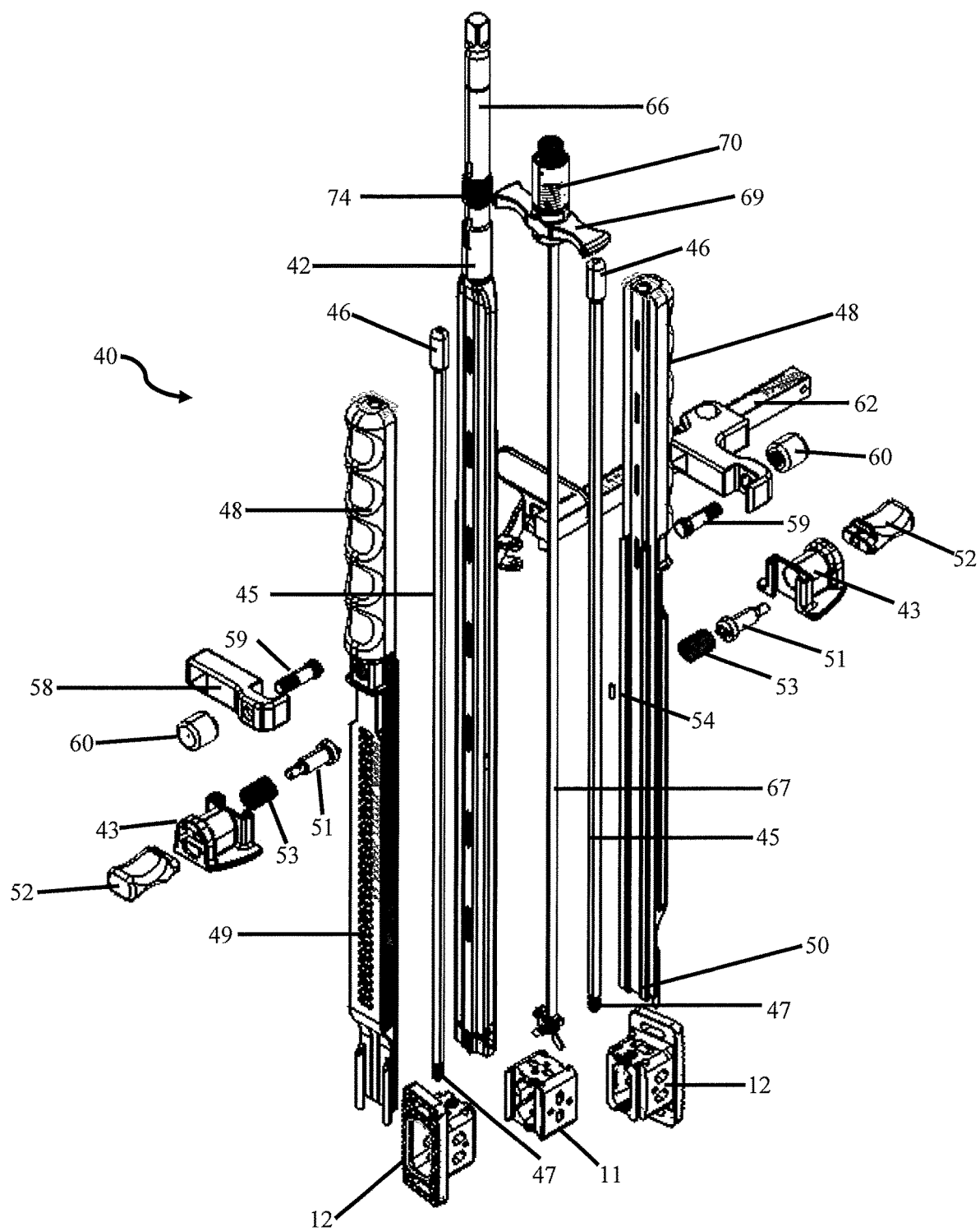
FIG. 17 is the exploded view of the lateral inserter assembly of FIG. 14.
Figure 18:
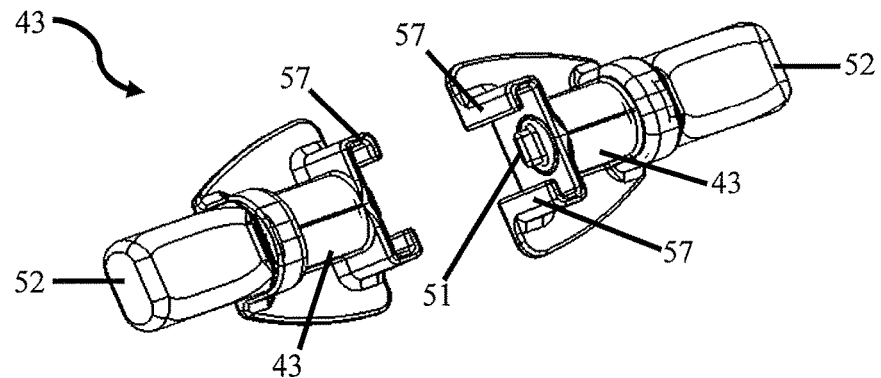
FIG. 18 is a perspective view of the bracket assembly of the lateral inserter assembly of FIG. 14.
Figure 19:
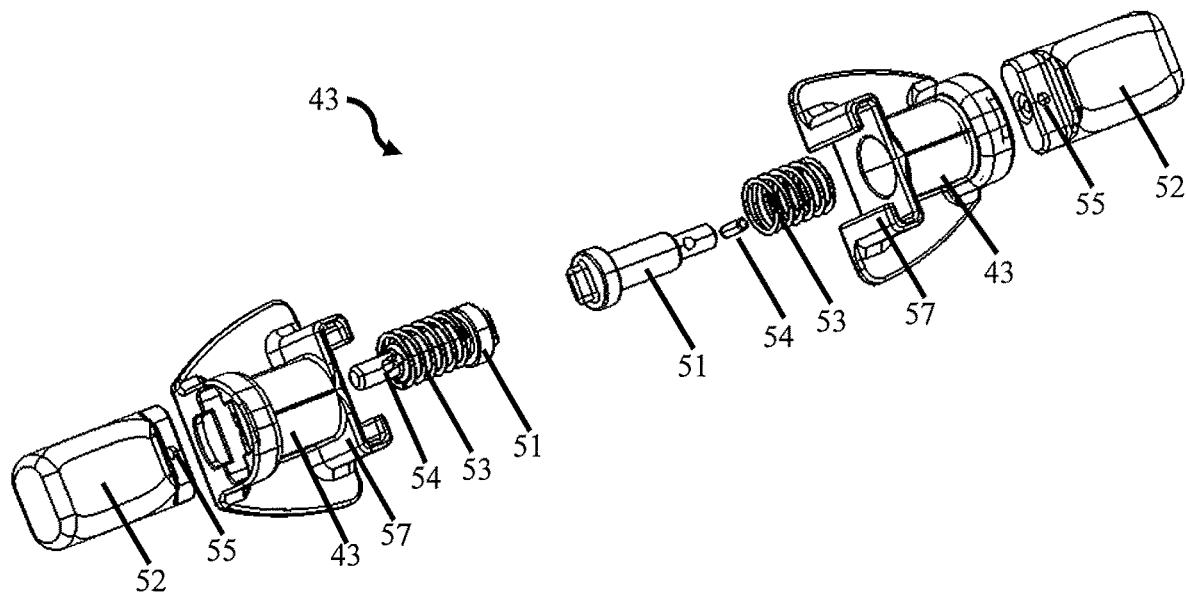
FIG. 19 is an exploded view of the bracket assembly of the lateral inserter assembly of FIG. 14.
Figure 20:
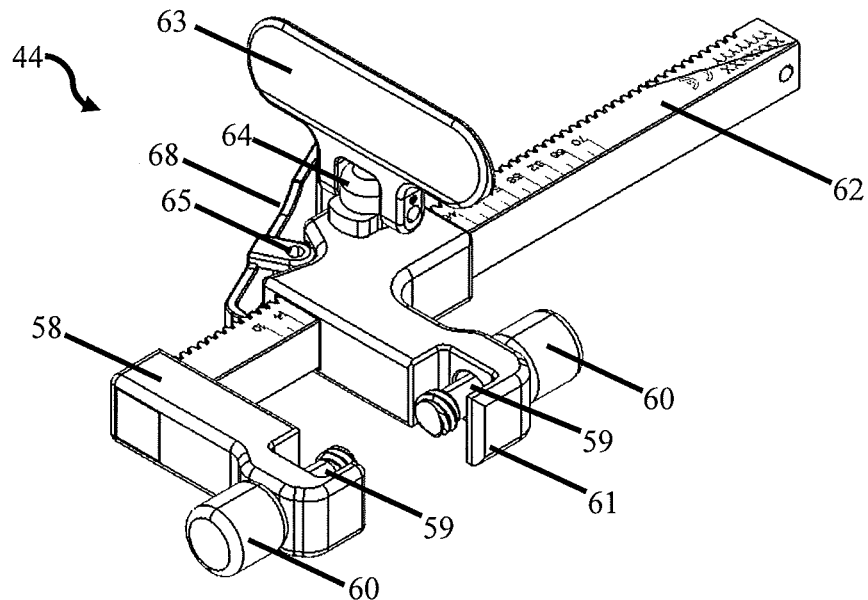
FIG. 20 is a perspective view of the clamp for the lateral inserter assembly of FIG. 14.
Figure 21:
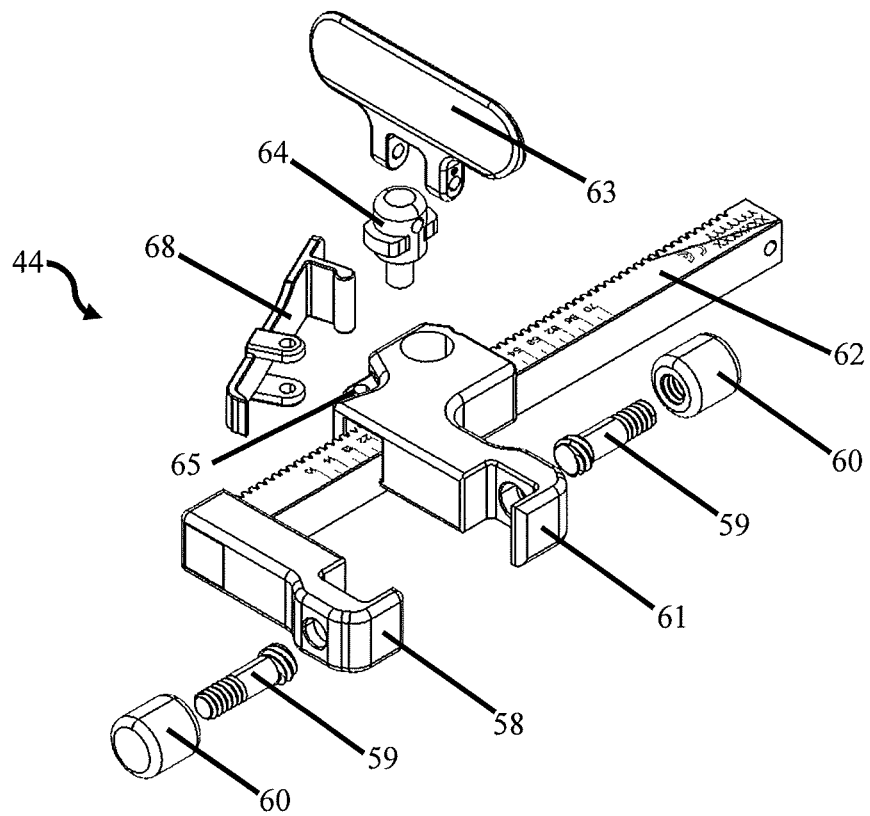
FIG. 21 is an exploded view of the clamp for the lateral inserter assembly of FIG. 14.
Figure 22:
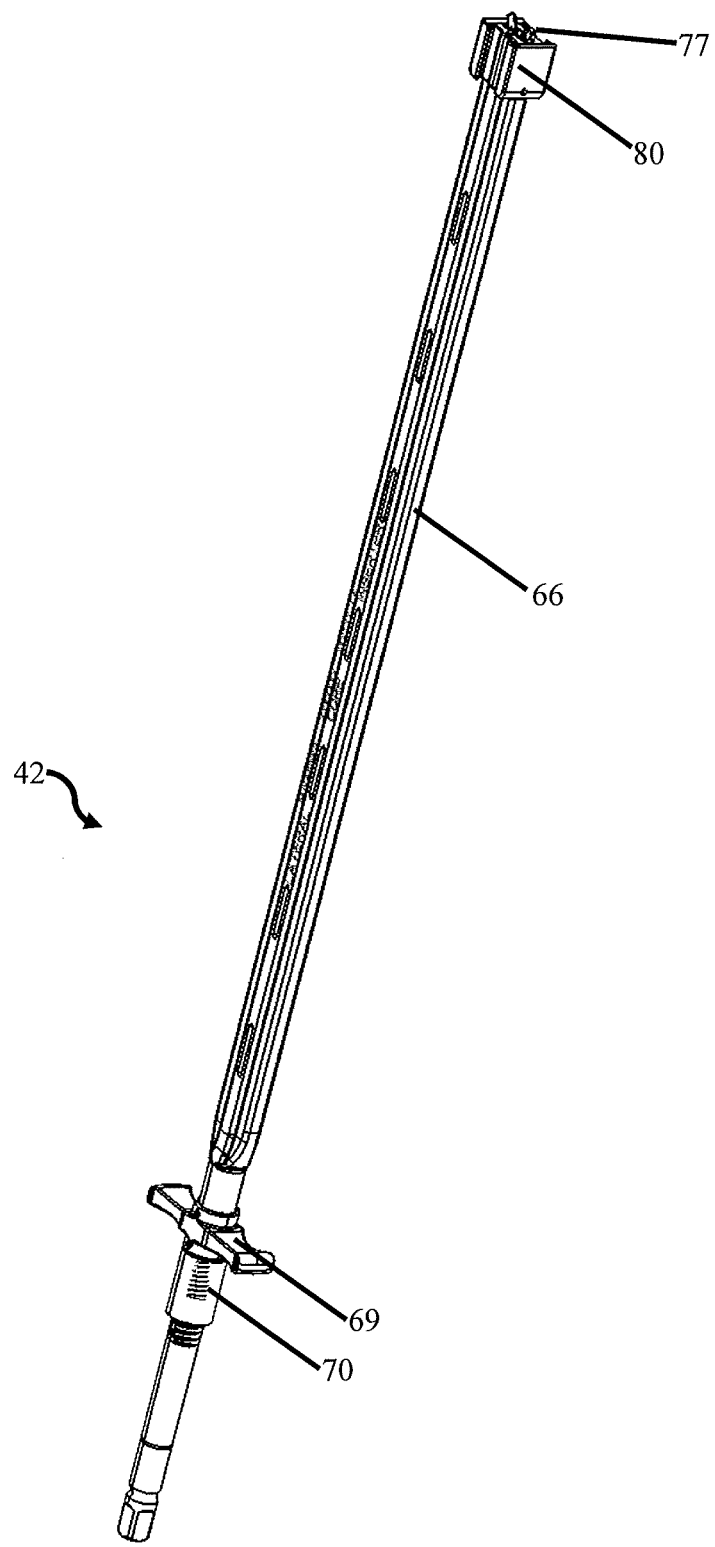
FIG. 22 is a perspective view of the core inserter assembly.
Figure 23:
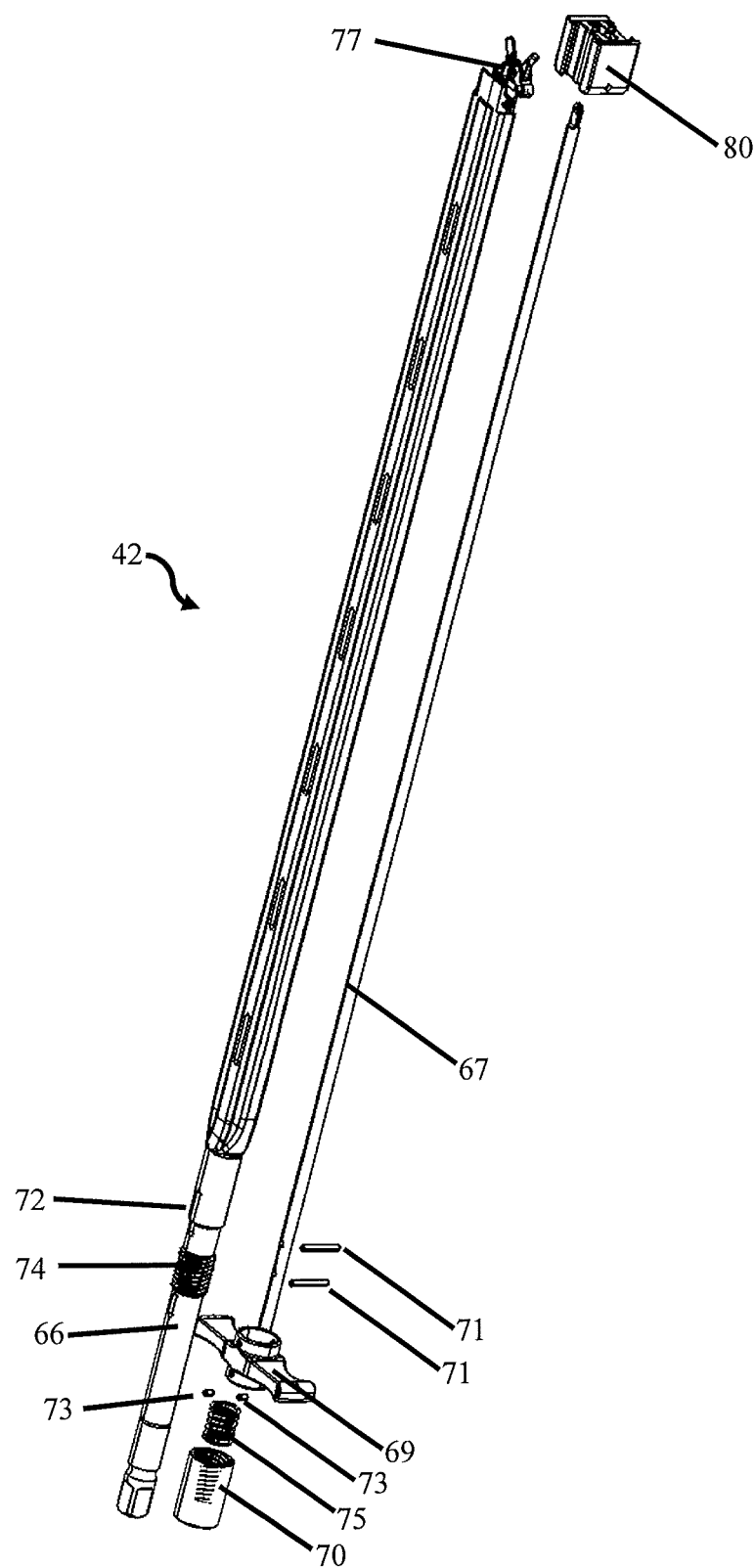
FIG. 23 is exploded view of the core inserter assembly of FIG. 22.
Figure 24:
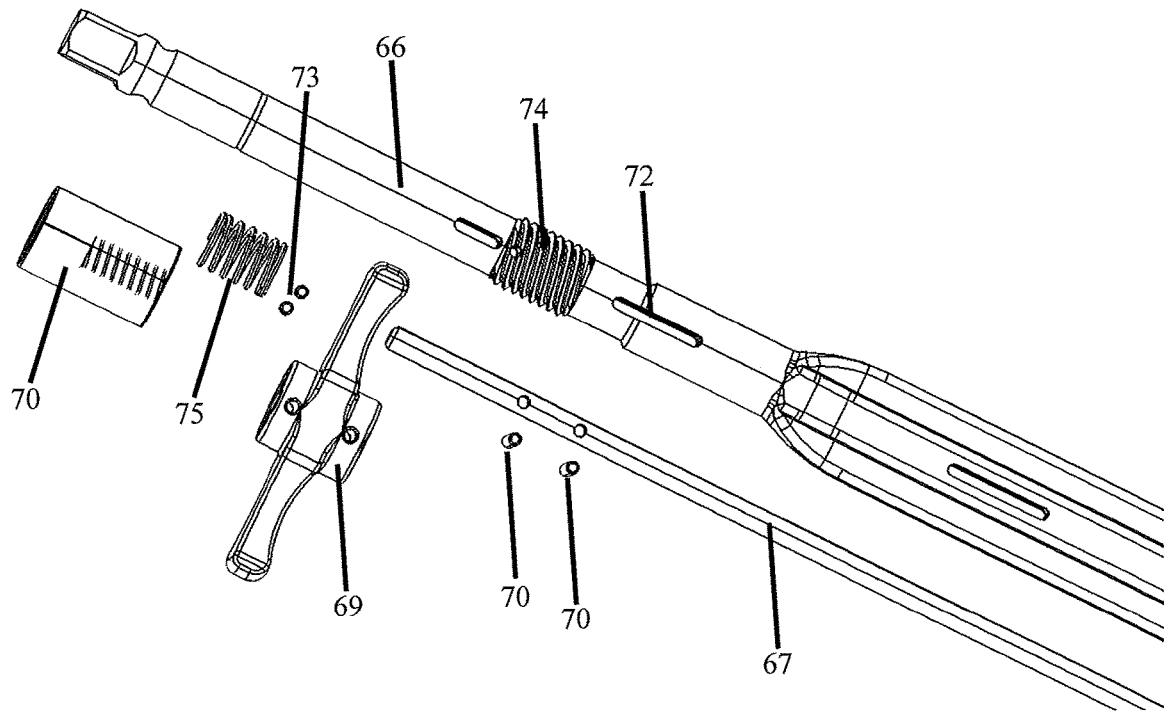
FIG. 24 is exploded view of top of core inserter assembly of FIG. 22.
Figure 25:
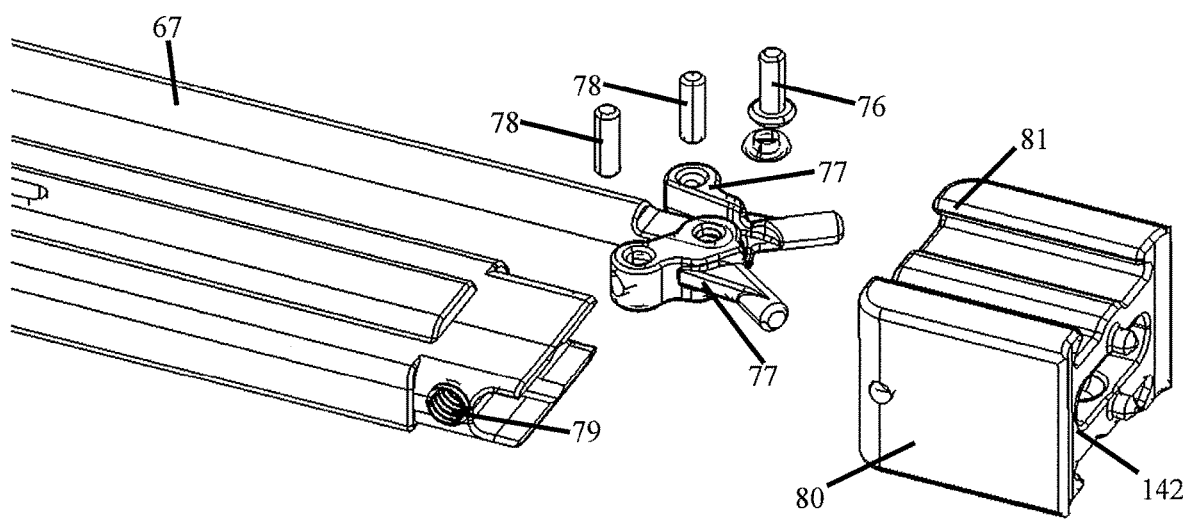
FIG. 25 is exploded view of bottom of core inserter assembly of FIG. 22.
Figure 26:
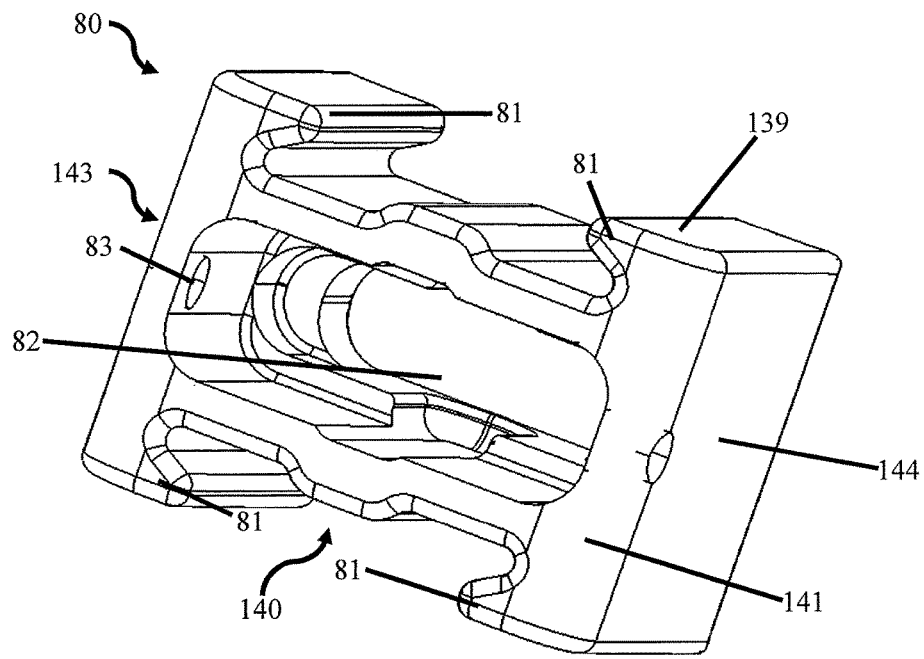
FIG. 26 is perspective view of distractor block of FIG. 22.

FIGS. 14-26 illustrate the lateral inserter system 40 according to one embodiment of the present invention. This embodiment of the lateral inserter system is comprised of two slide retainers 41, a core inserter 42, two bracket assemblies 43, and a clamp assembly 44.

The slide retainers 41 are constructed of a biocompatible material, such as stainless steel and are positioned on either side of the core inserter 42. Endcap retaining rods 45 are slid into the in the top of the slide retainer 41 and travel the complete length of the slide retainer 41. On the top of the endcap retaining rod 45 is a knurled knob 46 and the opposite end is a threaded end tip 47. The threaded end tip 47 can be attached to the top of the endcap 12 in screw hole 26. The front of the slide retainer 41 has a handgrip 48 to assist the surgeon in handling the device. Below the handgrip 48, on the front of the slide retainer 41 is a vertical height adjustment section 49. This vertical height adjustment section 49 allows varying height adjustment of the bracket assembly 43. On the inside of the slide retainer 41 is a mating section 50 which allows for coupling the core 11 onto the inside of the slide retainer 41 between the two endcaps 12.

The bracket assemblies 43 maintain position of the lateral inserter system 40 in the body during surgery. The vertical position of the bracket assembly 43 along the slide retainer 41 is adjustable in one embodiment by manually retracting the slide locks 51 by pulling the knobs 52 outward on the bracket assembly 43. The bracket assembly 43 is positioned vertically along the slide retainer 41 as required and the knobs 52 are released when in the desired position. In one embodiment, the slide locks 51 are held extended in the locked position by the extension force of a spring 53 inside the bracket assembly 43. Here, the slide lock 51 is affixed to the knob 52 by a pin 54 inserted through a hole 55 in the knob and a hole 56 in the top of the slide lock 51. The inside edges 57 of the bracket assembly 43 are curved to allow the bracket assembly 43 to move along the outside edges of the slide retainer 41.

The clamp assembly 44 allows for both measuring the space between vertebral bodies in the spine and maintaining the proper space between the slide retainers 41 during lateral insertion. The clamp assembly 44 is made of a biocompatible material, such as stainless steel. The upper arm 58 of the clamp assembly 44 is affixed to the slide retainer 41 by means such as a screw 59 and a retaining nut 60. The lower arm 61 of the clamp assembly is attached to the opposite slide retainer 41 in similar fashion. The measurement bar 62 is mounted into the end of the upper arm 58 opposite the slide retainer 41 attachment point. The lower arm 61 travels along the measurement bar 62 with the opposite end affixed to the slide retainer mount 41. The lower arm 61 is held in place by a locking device 68 which is attached to the lower arm 41 by the mounting pin 65. A handle 63 is attached to a locking screw 64 inside the lower arm. Turning the handle 63 engages and disengages the locking device 68, restricting and allowing travel of the lower arm 41 along the measurement bar 62 which changes the distance between the slide retainers 41.

The core inserter 42 is made of biocompatible material, such as stainless steel. In one embodiment, the core inserter 42 comprises an outer container 66, an inner rod 67, a core distractor block 80, a quick release 69 and a locking nut 70. The inner rod 67 slides within the hollow outer container 66 and is attached at the upper end by release pins 71 which travel through holes in the inner rod and into slots 72 in the outer container which limit the travel of the rod. The quick-release 69 fits around and is attached to the outer container 66 by two lock pins 73. The inside of the locking nut 70 is threaded and fits around the outer container 66 and screws onto the threaded area 74 on the outside of the container. A spring 75 fits around the outer container 66 between the quick-release 69 and the locking nut 70. The spring 75 is compressed and the force on the spring is translated as a downward force on the inner rod 67, keeping the arms 77 at the end of the core inserter 42 extended unless upward force is applied to the quick-release 69 counteracting spring 75 force. The lower end of the inner rod 67 is attached to the center pin 76 holding the core inserter arms 77 together. Two pivot pins 78 allow the core inserter arms 77 to pivot around the center pin 76, opening and closing the arms.

With the core inserter arms 77 together, the outer container 66 slides into the distractor block 80. The distractor block 80 is made of biocompatible material. For example, the components may be machined from implantation-grade polyether ether ketone (PEEK). The distractor block 80 is held onto the core inserter 42, in one case, by two ball detents 78 on both sides of the core inserter 42. The top 139 and bottom sides 139 of the distractor block 80 have a mating section with connectors 81 which are smaller than those of the center core 11 in order to take the downward load off the core 11 during distraction. The center of the distractor block 80 is hollow to allow the bottom of the outer container 66 to slide into and attach to the distractor block 80. On the inside of the left 143 and right 144 sides of the distractor block 80 are recessed holes 83 where the ball detents 79 from the outer container 66 meet with and attach the distractor block 80 to the outer container 66. Pulling the distractor block 80 vertically down off the outer container 66 will release the ball detents 79, allowing the distractor block 80 to be removed from the outer container 66.

Figure 27:
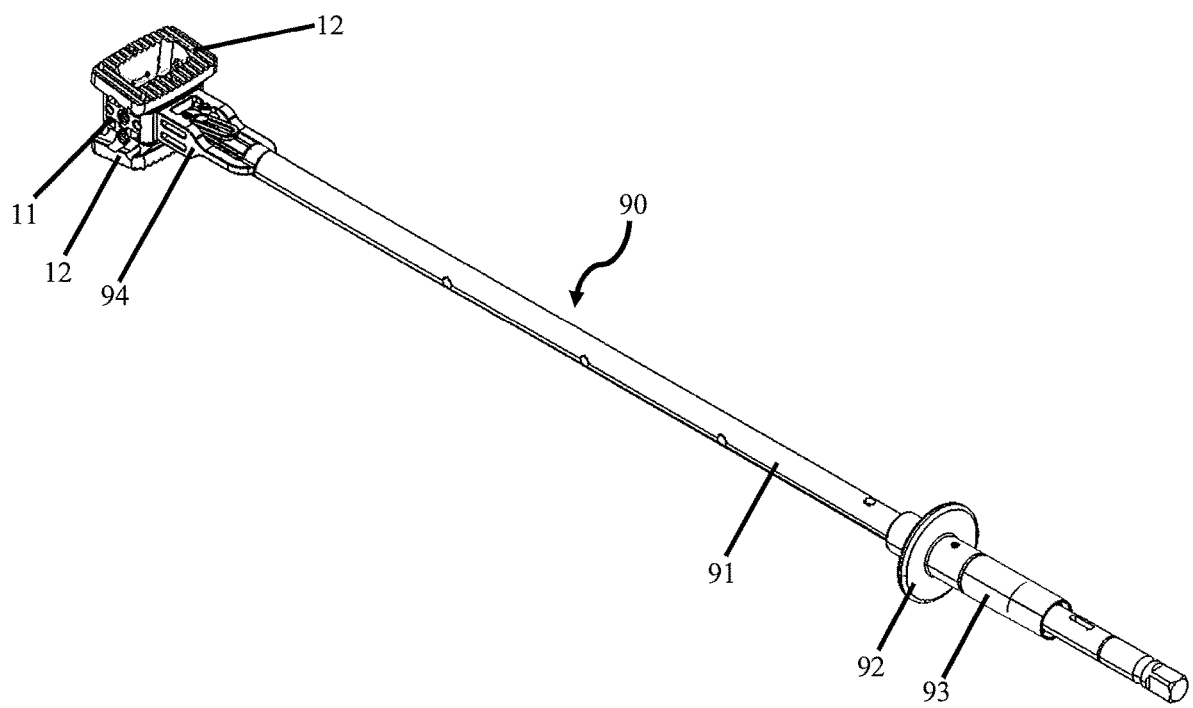
FIG. 27 is a perspective view of anterior inserter assembly.
Figure 28:
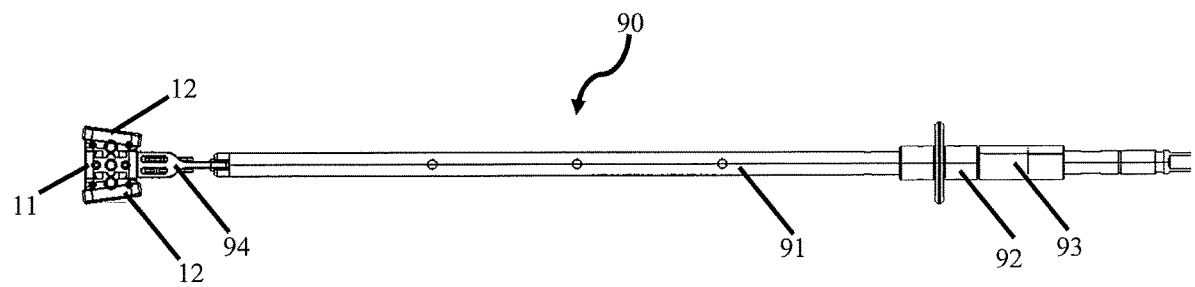
FIG. 28 is side view of anterior inserter assembly of FIG. 27.
Figure 29:
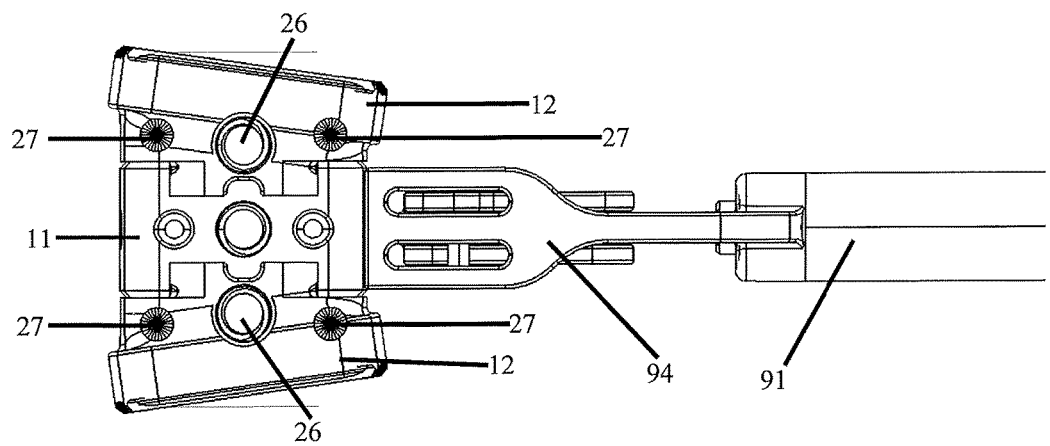
FIG. 29 is detailed view of bottom end of anterior inserter assembly of FIG. 27.
Figure 30:
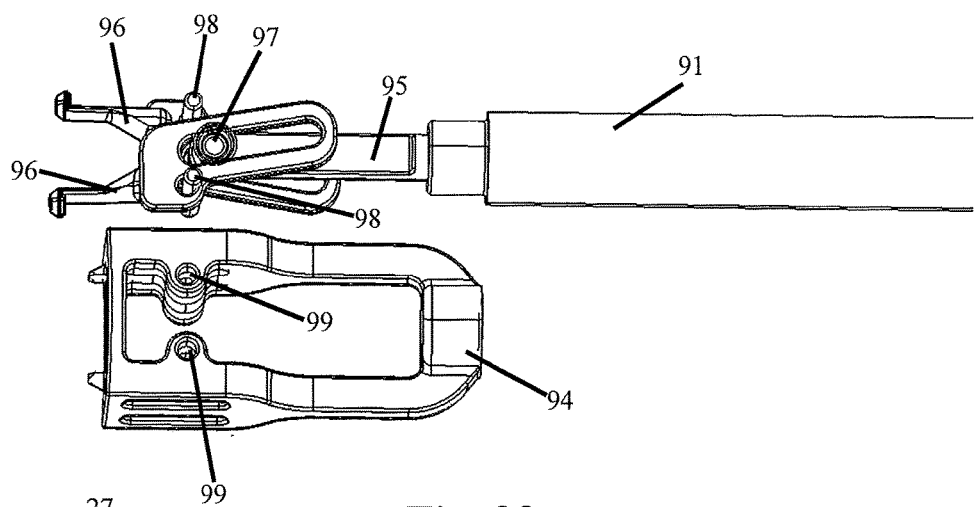
FIG. 30 is an exploded view of the bottom end of the anterior inserter assembly of FIG. 27.
Figure 31:
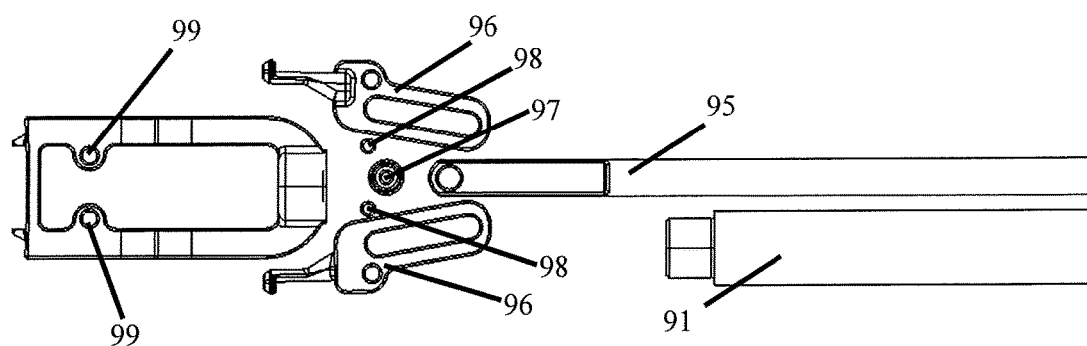
FIG. 31 is further exploded view of the bottom end of the anterior inserter assembly of FIG. 27.
Figure 32:
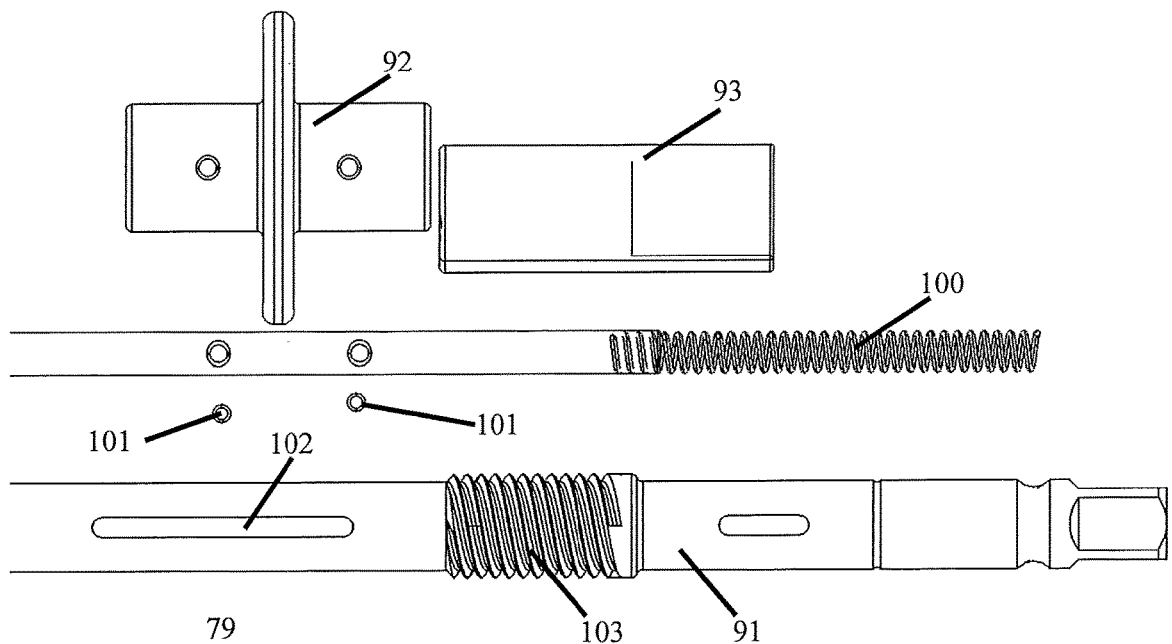
FIG. 32 is an exploded view of the top end of the anterior inserter assembly of FIG. 27.

FIGS. 27-32 illustrate the anterior inserter system 90 according to one embodiment of the present invention. The anterior inserter system 90 is comprised of a hollow outer container 91 a collet 92, a lock 93, a bracket assembly 94, an inner shaft 95 and two bracket arms 96 which attach to the center core 11. The anterior inserter system 90 is constructed from biocompatible material, such as stainless steel. The end of the bracket aims 96 are machined to enable them to affix to the core 11 by traveling through holes 20 on the core 11 and grasping the inside edge of the core material. Both bracket arms 96 are connected to the end of the inner shaft 95 by means such as a center pin 97. The bracket arms 96 are also connected to the bracket 94 by two pivot pins 98. The bracket assembly 94 allows vertical movement of the inner shaft 95, which pivots the bracket arms 96 around the pivot pins 98 causing the bracket arms 96 to open and close.

The pivot pins travel through holes 99 on the bracket 94 which affix the bracket arms 96 to the bracket assembly 94.

At the opposite end of the anterior inserter system 90 from the bracket assembly 94 is the release assembly. The release assembly is comprised of the collet 92, a lock 93 a spring 100 and two release pins 101. The release pins 101 go through the top of the inner shaft 95 and through slots 102 in the outer container 91. The release pins 101 ride in the slots 102 allowing for some limited, vertical movement of the inner shaft 95 within the outer container 91. A spring 100 is placed on the inside of the outer container 91 at the end, between the end of the outer container 90 and the end of the inner shaft 95 allowing for tension being placed upon the inner shaft 95. The force of the spring 100 causes downward force on the inner shaft 95 which causes the bracket arms 96 to pivot around the pivot pins 98 and the bracket anus 96 to spread out. The spread bracket arms 96 of the anterior inserter 90 affix the center core 11 to the anterior inserter 90. Upward force on the collet 92, causes the inner shaft 95 to move upwards, causing the bracket arms 96 to move toward the center (retract), allowing the anterior inserter system 90 to be removed from the center core 11 after being property positioned in the body. The outer container 91 is travels through the hole in the center of the collet 92 and the collet 92 is affixed to the outer container 91 by the release pins 101 which travel through the collet 92, the outer container 91 and inner shaft 95. Located just above the collet 92 on the outer container is a threaded area 103. The inside of the lock 93 is threaded. The top of the outer container 91 is placed through the center of the lock 93. The lock 93 is then screwed onto the outer container 91 onto the threaded area 103 until it meets the edge of the collet 92. The lock 93 is used to maintain the collet 92 in the desired position during insertion of the vertebral body replacement. Adjusting the position of the lock 93 on the threaded area 103 allows for movement in the collet 92 on the outer container 91.

Figure 33:
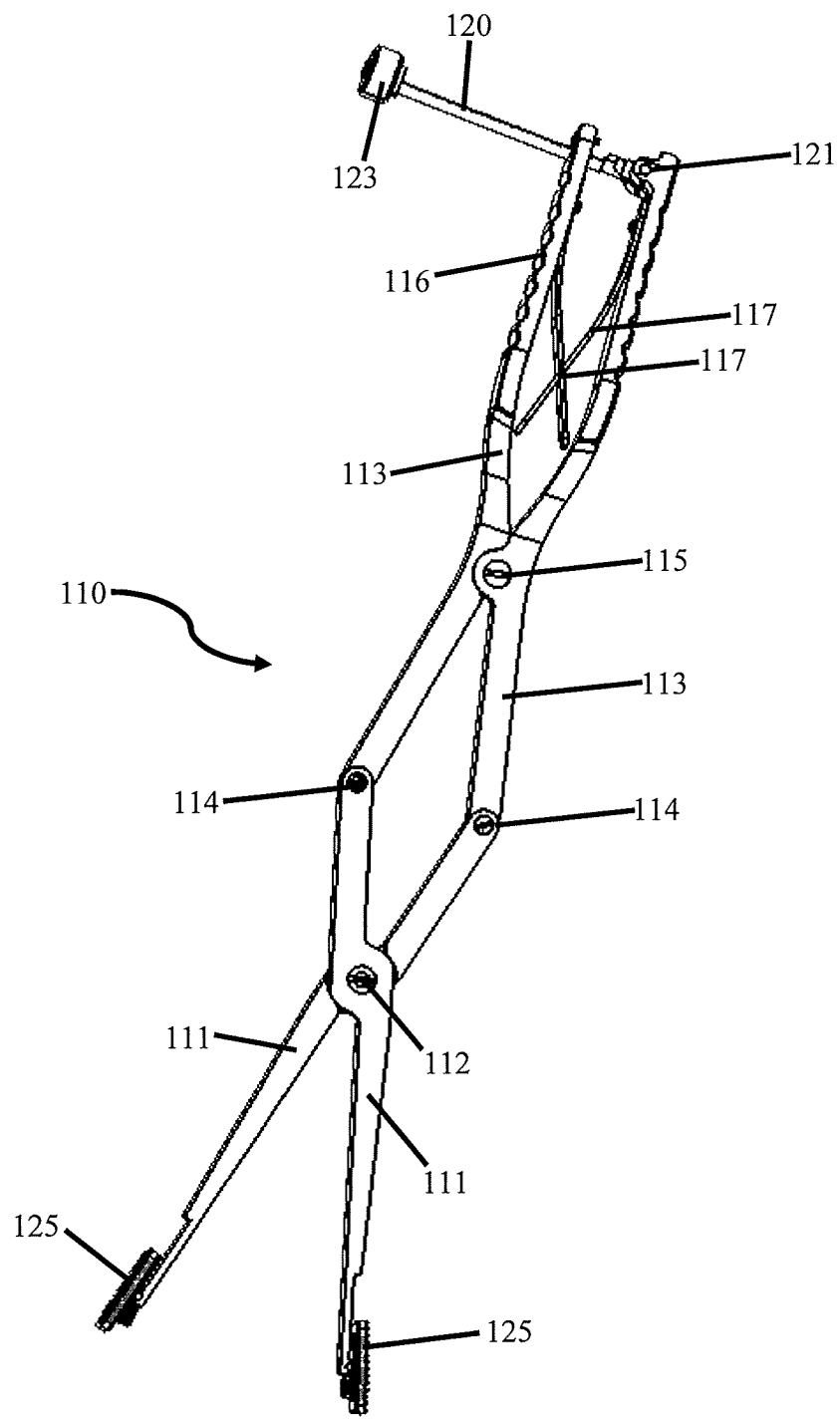
FIG. 33 is a perspective view on the distractor/sizer assembly.
Figure 34:
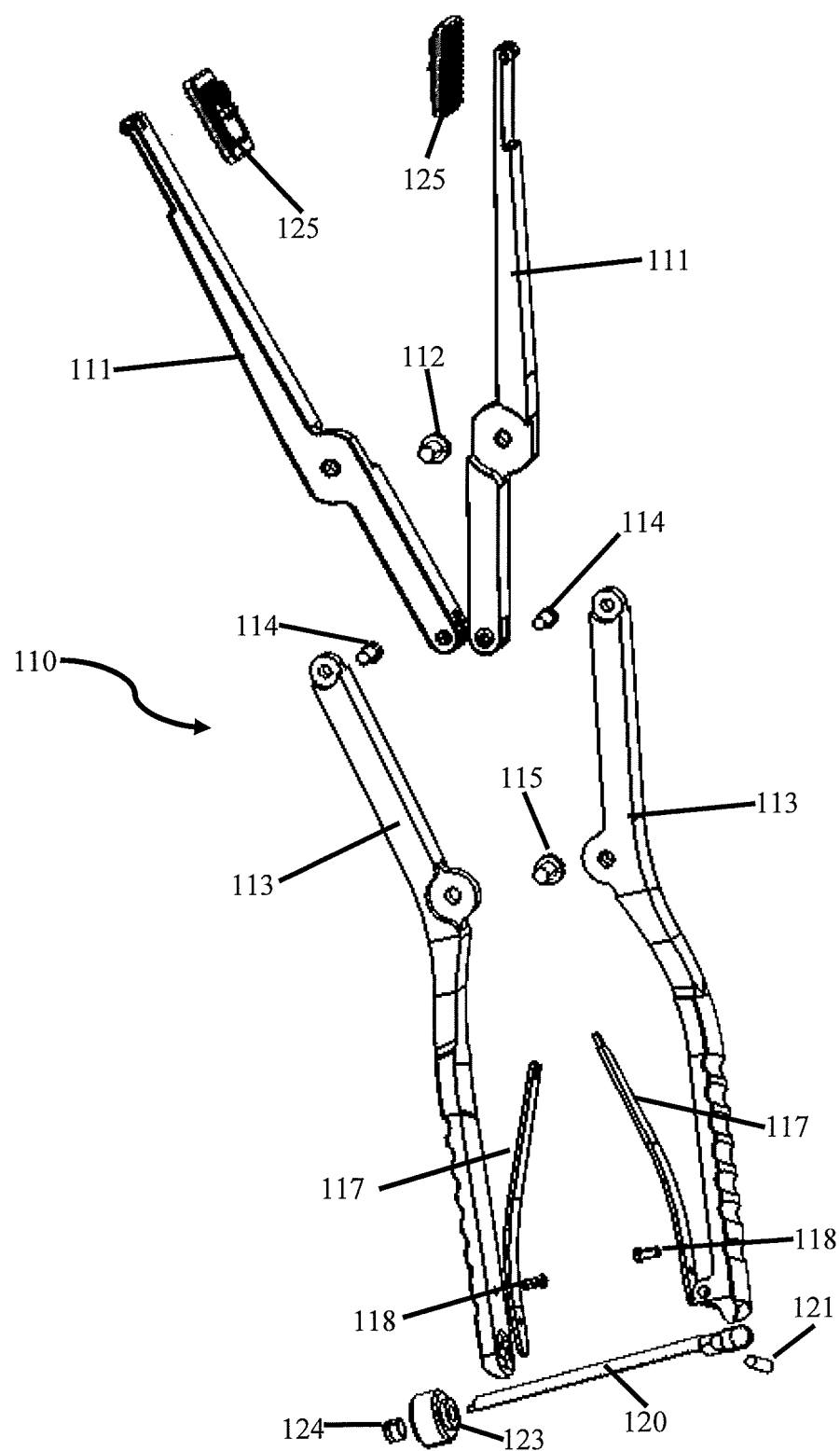
FIG. 34 is an exploded view of the distractor/sizer assembly of FIG. 33.
Figure 35:
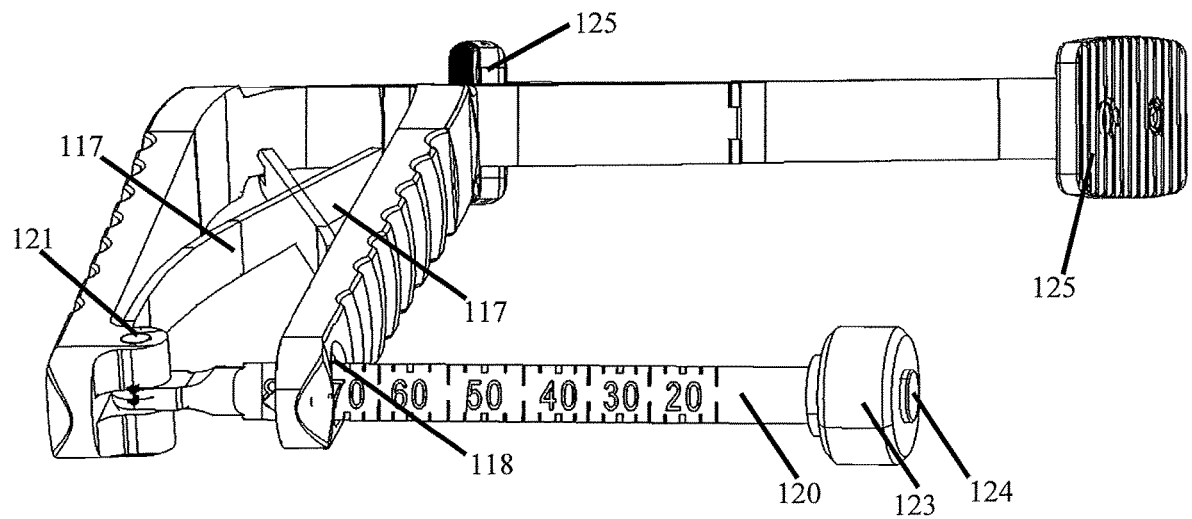
FIG. 35 is a bottom view of the distractor/sizer assembly of FIG. 33.
Figure 36:
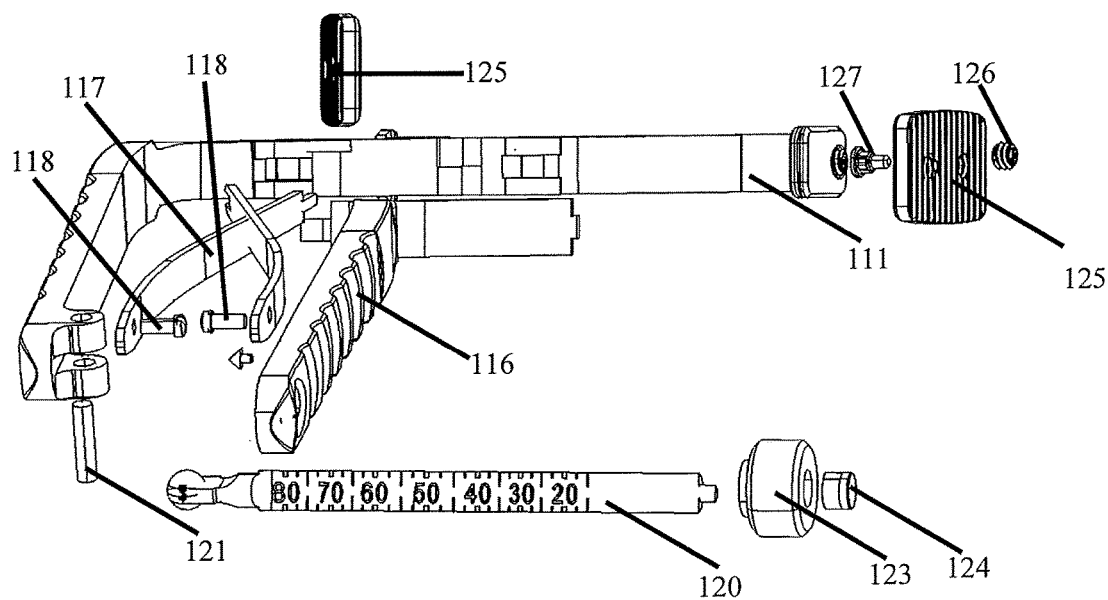
FIG. 36 is an exploded view of the bottom of the distractor/sizer assembly of FIG. 33.
Figure 37:
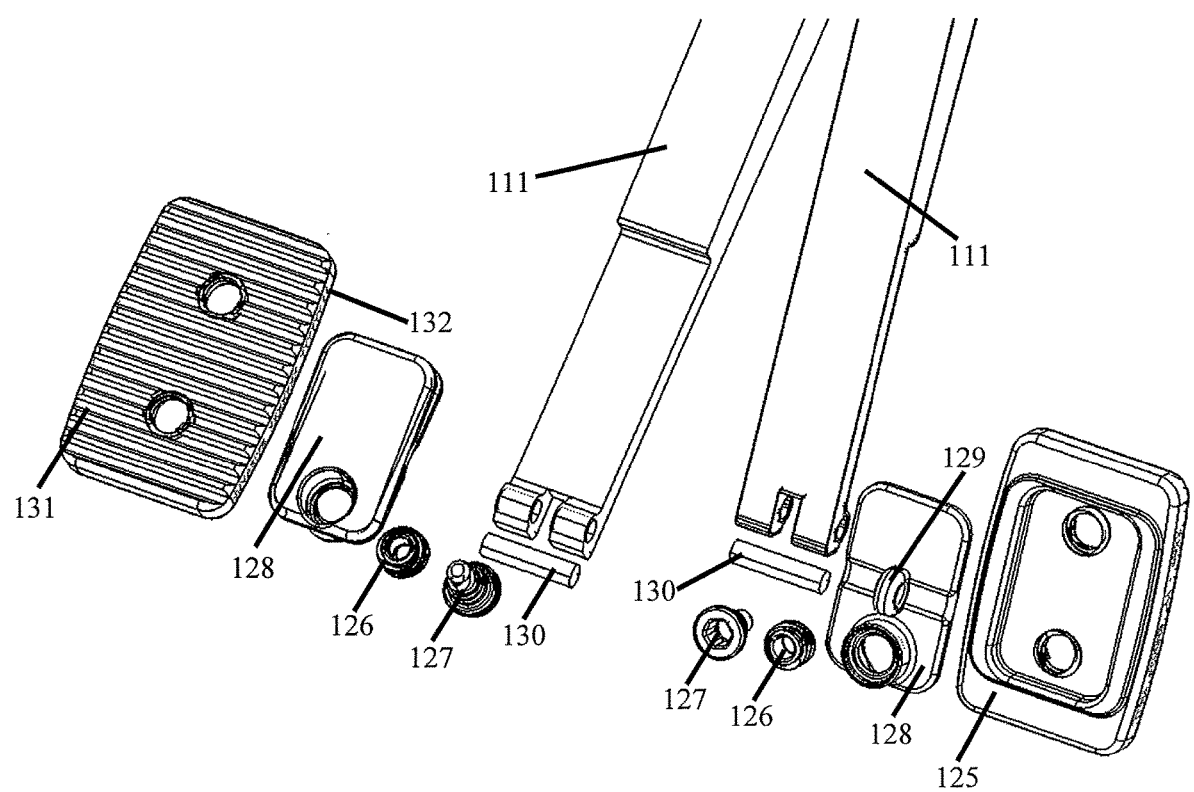
FIG. 37 is a detailed view of the bottom of the distractor/sizer assembly of FIG. 33.
Figure 38:
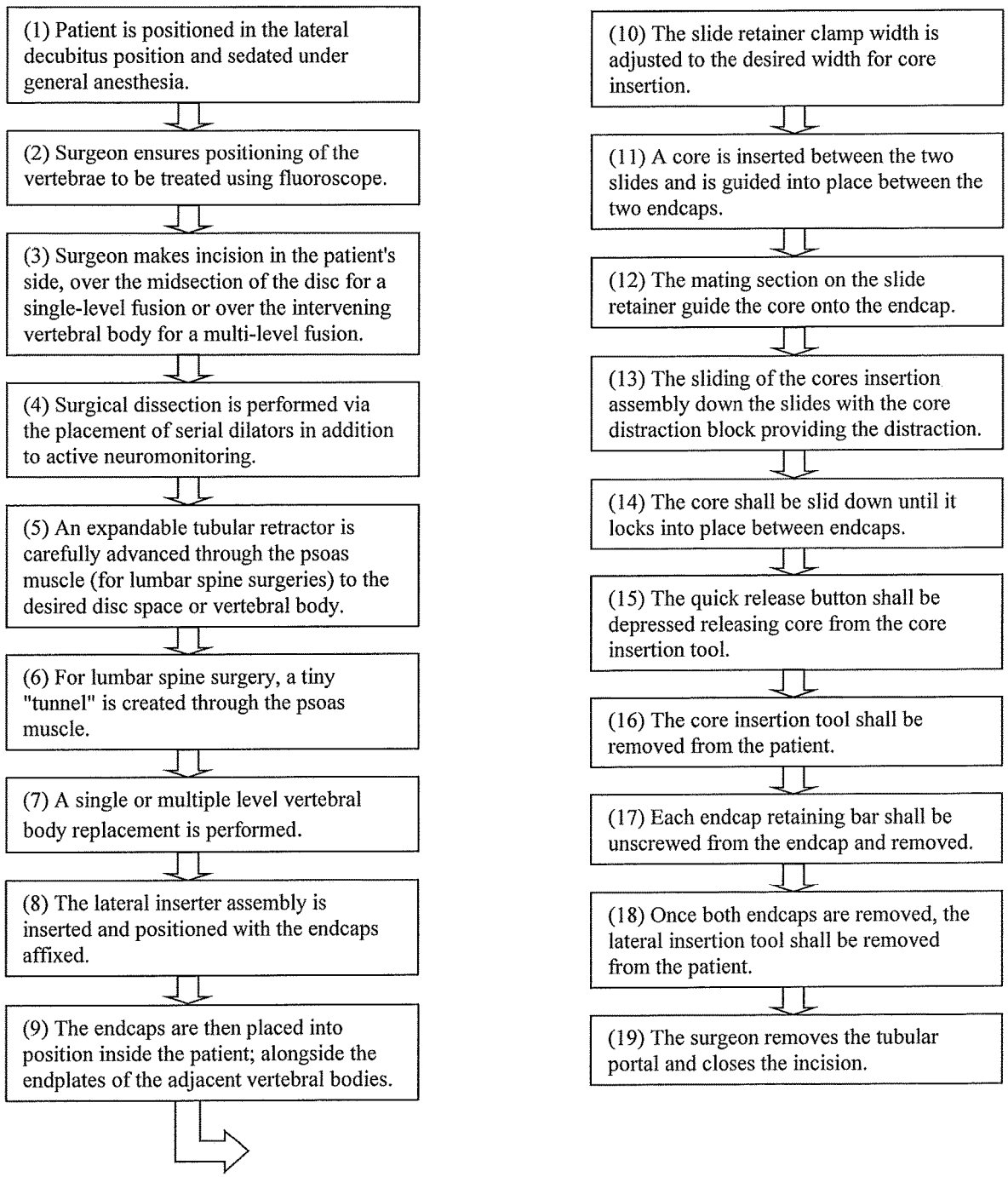
FIG. 38 illustrates the steps involved in using the lateral inserter assembly.
Figure 39:
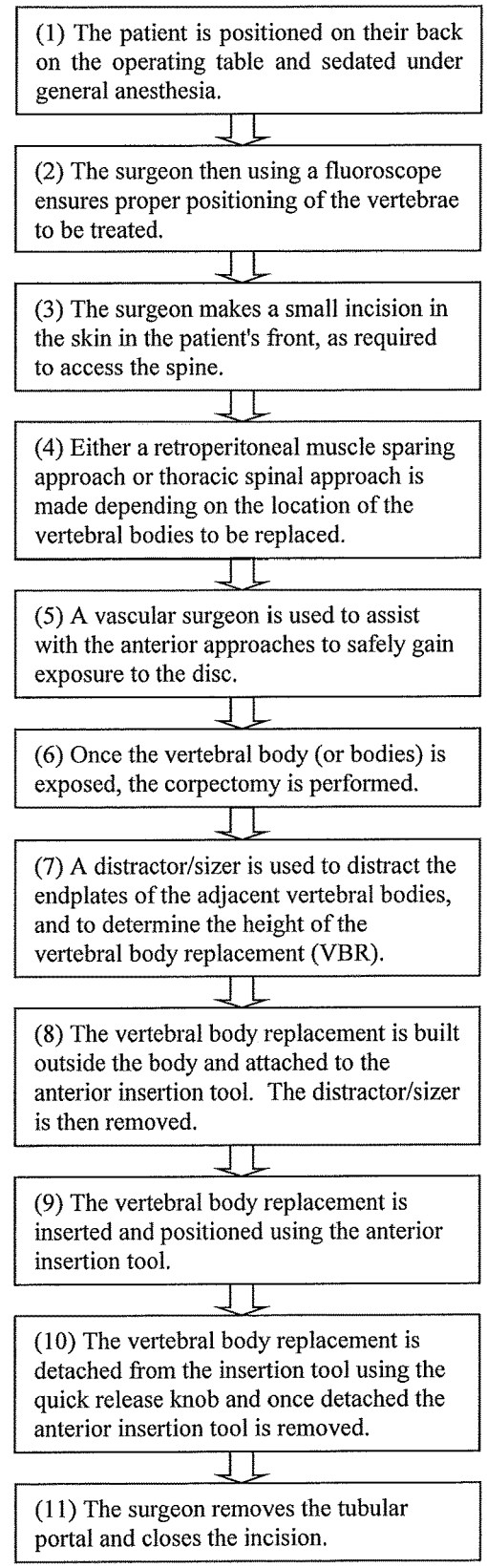
FIG. 39 illustrates the steps involved in using the anterior inserter assembly.

FIGS. 33-37 illustrate the distractor/sizer 110 according to one embodiment of the present invention. The distractor/sizer 110 is constructed from a biocompatible material such as stainless steel and is comprised of lower arms 111 held together in the center of the arm by the lower center screw 112. The top of the lower arms 111 are affixed to the bottom of the upper arms 113 by two screws 114. The upper arms 113 pivot around the upper center screw 115. The outer edges of the upper arms 113 are curved to form a handgrip 116. A pair of flexible bars 117 are affixed between the upper arms 113 by mounting pins 118. The flexible bars 117 hold the upper arms 113 apart and provide some resistance as the upper arms 113 are closed together. As the upper arms 113 are moved together (closed), the bottom end of the upper arms 113 move apart. This movement causes the upper end of the lower arms 111 to move apart and the bottom of the lower arms 111 with the endplates 119 to move apart, causing distraction. A measurement bar 120 is affixed to one end of the upper arms 113 by a mounting pin 121. The other end of the measurement bar 120 travels through a hole 122 on the other upper arm 113. A collar 123 is attached to the end of the measurement bar 120 by an endcap 124 affixed to the end of the measurement bar 120. The endplates 125 are affixed by threaded screws 126 and caps 127 to endcap brackets 128 which have an attaching point 129 which affix the endcap brackets 128 to the bottom end of the lower arms 111 via a pivot pin 130. The outside edges of the endplates 125 have anti-migration elements 131 to maintain the proper position of the distractor/sizer 110 on the vertebral bodies during distraction. The measurement bar 120 is calibrated to allow the surgeon to determine the size of vertebral body replacement required for the patient. The distractor/sizer 110 allows for distraction and sizing to be completed with one surgical tool.

While the invention is susceptible to various modifications and alternative forms, specific embodiments thereof have been shown by way of example in the drawings and are herein described in detail. It should be understood, however, that the description herein of specific embodiments is not intended to limit the invention to the particular forms disclosed, but on the contrary, the invention is to cover all modifications, equivalents, and alternatives falling within the spirit and scope of the invention as defined herein.

What is claimed is:

1. A method for implanting a vertebral body replacement device in a space between a first and a second vertebrae, the method comprising:
    generating lateral access through a psoas muscle of a subject to a space between the first and the second vertebrae;
    attaching a first endcap and a second endcap of the vertebral body replacement device to a distal end of an inserter assembly;
    inserting the first endcap and the second endcap into the space between the first and the second vertebrae via the lateral access using the inserter assembly; and
    inserting a central core laterally between the first endcap and the second endcap by coupling a superior mating feature of the central core to a first mating feature of the first endcap and an inferior mating feature of the central core to a second mating feature of the second endcap using a core inserter of the inserter assembly.

2. The method of claim 1, wherein inserting the central core laterally between the first endcap and the second endcap comprises inserting the central core until the central core locks into place between the first endcap and the second endcap.

3. The method of claim 1, further comprising releasing the central core from the inserter assembly, and removing the core inserter of the inserter assembly.

4. The method of claim 3, further comprising releasing the first endcap and the second endcap from the inserter assembly, and removing the inserter assembly from the subject, subsequent to removing the core inserter.

5. The method of claim 1, further comprising adjusting a width between the first endcap and the second endcap subsequent to inserting the first endcap and the second endcap based on a width of the central core to be inserted, by adjusting a space between a first slide retainer and a second slide retainer using a clamp assembly affixed to each of the first and the second slide retainers.

6. The method of claim 5, wherein the clamp assembly comprises a handle, and the method further comprises turning the handle to limit or to allow movement of the first or the second slide retainer, thereby adjusting a width of the space between the first slide retainer and the second slide retainer.

7. The method of claim 1, further comprising measuring a width of the space between the first and the second vertebrae and maintaining the width during insertion of the central core using a clamp assembly affixed to each of a first and a second slide retainer.

8. The method of claim 1, wherein attaching the first endcap and the second endcap to the distal end of the inserter assembly comprises attaching each of the first endcap and the second endcap to a corresponding threaded end tip of the inserter assembly.

9. The method of claim 1, wherein attaching the first endcap and the second endcap of the vertebral body replacement device to the distal end of the inserter assembly comprises attaching a first side of the first endcap to a first slide retainer and a first side of the second endcap to a second slide retainer of the inserter assembly.

10. The method of claim 9, further comprising attaching the central core to the core inserter and slideably coupling the central core to the first and the second slide retainers.

11. The method of claim 10, wherein inserting the central core laterally between the first endcap and the second endcap comprises sliding the central core distally relative to the first slide retainer and the second slide retainer.

12. The method of claim 1, wherein a first side of the first endcap is opposing and parallel to a second side of the first endcap.

13. The method of claim 1, wherein the superior mating feature, the inferior mating feature, or both extends in a lateral direction from a first side to a second side of the first endcap, and wherein one or both of the superior mating feature and the inferior mating feature comprise two grooves or flanges opposing each other and extending in parallel.

14. The method of claim 1, wherein the central core comprises a maximum length along a lateral direction that is less than a maximum length of the first endcap or the second endcap.

15. The method of claim 1, wherein the central core comprises a maximum height along a direction perpendicular to a lateral direction that is less than a maximum height of the first endcap or the second endcap.

16. A method for implanting a vertebral body replacement device in a space between a first and a second vertebrae, the method comprising:
    generating lateral access through a psoas muscle of a subject to a space between the first and the second vertebrae;
    attaching a first endcap to a first slide retainer and a second endcap to a second slide retainer of an inserter assembly;
    inserting the first endcap and the second endcap into the space between the first and the second vertebrae via the lateral access using the inserter assembly; and
    attaching a central core to a core inserter of the inserter assembly and slideably coupling the central core to the first and the second slide retainers; and
    inserting the central core laterally between the first endcap and the second endcap, the inserting including coupling a superior mating feature of the central core to a first mating feature of the first endcap, and an inferior mating feature of the central core to a second mating surface of the second endcap using the core inserter of the inserter assembly.

17. The method of claim 16, wherein inserting the central core laterally between the first endcap and the second endcap comprises sliding the central core distally relative to the first and the second slide retainers onto the first endcap and the second endcap until the central core locks into place between the first endcap and the second endcap.

18. A method for implanting a vertebral body replacement device in a space between a first and a second vertebrae, the method comprising:
    providing an inserter assembly to a user;
    providing the vertebral body replacement device configured to be attached to a distal end of the inserter assembly, the vertebral body replacement device comprising:
    a first endcap having a first mating feature;

a second endcap having a second mating feature; and
a central core having a superior mating feature configured to couple to the first mating feature of the first endcap, and an inferior mating feature configured to couple to the second mating feature of the second endcap;

inserting the first endcap and the second endcap between the first and the second vertebrae; and inserting the central core laterally via a lateral access through a psoas muscle of a subject, wherein the central core is disposed between the first endcap and the second endcap.

19. The method of claim 18, wherein the first endcap comprises a first side that is configured to attach to the distal end of the inserter assembly, and a second side opposing and parallel to the first side.

20. The method of claim 18, wherein the superior mating feature, the inferior mating feature, or both extends in a lateral direction from a first side to a second side of the first endcap, and
wherein one or both of the superior mating feature and the inferior mating feature comprise two grooves or flanges opposing each other and extending in parallel.

\* \* \* \* \*